United States Patent
Satoh et al.

(10) Patent No.: US 6,341,520 B1
(45) Date of Patent: Jan. 29, 2002

(54) METHOD AND APPARATUS FOR ANALYZING BREATH SAMPLE

(75) Inventors: Katsuhiko Satoh; Akira Yanagida, both of Shizuoka (JP); Akira Takenaka, c/o Yamada-cho, Kitashirakawa, Sakyo-ku, Kyoto, Kyoto-fu (JP)

(73) Assignees: Suzuki Motor Corporation, Shizuoka; Akira Takenaka, Kyoto-fu, both of (JP)

(*) Notice: Subject to any disclaimer, the term of this patent is extended or adjusted under 35 U.S.C. 154(b) by 0 days.

(21) Appl. No.: 09/665,058

(22) Filed: Sep. 19, 2000

Related U.S. Application Data

(62) Division of application No. 08/910,113, filed on Aug. 13, 1997, now Pat. No. 6,148,657.

(30) Foreign Application Priority Data

Aug. 13, 1996 (JP) .............................. 8-231371
Aug. 13, 1996 (JP) .............................. 8-231372
May 20, 1997 (JP) .............................. 9-145846

(51) Int. Cl.$^7$ .......................... G01N 1/00; G01N 25/02; B01D 15/08
(52) U.S. Cl. .................... 73/23.35; 73/23.41; 73/23.42; 422/84; 422/89; 95/87; 600/532
(58) Field of Search .................... 422/84, 89; 436/900; 73/23.36, 23.41, 23.42; 95/87; 600/529, 532

(56) References Cited

U.S. PATENT DOCUMENTS

| | | | |
|---|---|---|---|
| 3,753,656 A | * 8/1973 | Matson et al. ................ 73/23.1 |
| 3,915,013 A | * 10/1975 | Gaeke ......................... 73/422 |
| 3,970,561 A | 7/1976 | Sievers et al. .......... 210/198 C |
| 4,133,640 A | * 1/1979 | Clinton et al. ................. 23/230 |
| 4,257,772 A | 3/1981 | Bognin et al. .......... 23/230 PC |
| 4,849,179 A | 7/1989 | Reinhardt et al. ............. 422/89 |
| 5,108,466 A | 4/1992 | Klein et al. ..................... 55/20 |
| 5,425,374 A | 6/1995 | Ueda et al. ................. 128/719 |
| 5,458,853 A | 10/1995 | Porter et al. ................... 422/84 |
| 5,465,728 A | 11/1995 | Phillips ....................... 128/730 |
| 5,547,497 A | * 8/1996 | Klemp et al. .................. 96/104 |
| 5,573,005 A | 11/1996 | Ueda et al. ................. 128/730 |
| 5,611,846 A | * 3/1997 | Overton et al. ................ 96/102 |
| 5,804,142 A | 9/1998 | Ito et al. ....................... 422/70 |
| 5,847,291 A | * 12/1998 | Green et al. ............. 73/863.33 |

FOREIGN PATENT DOCUMENTS

| | | |
|---|---|---|
| JP | 9-89863 | 4/1997 |
| JP | 9138225 | 5/1997 |
| JP | 9243627 | 9/1997 |
| JP | 1019865 | 1/1998 |

* cited by examiner

*Primary Examiner*—Hezron Williams
*Assistant Examiner*—David J. Wiggins
(74) *Attorney, Agent, or Firm*—Greenblum & Bernstein P.L.C.

(57) ABSTRACT

Method and apparatus for analyzing a breath sample provide user-friendly operation and analysis. The method and apparatus provide automatic operation and coordination of operation of an absorbent sample tube, including desorbing means, a chromatographic precolumn, a chromatographic main column, a detector, a data processor, a sample receiving tube for receiving exhaled breath sample, a sample loop for aspirating a prescribed quantity of breath sample from the sample receiving tube, a sample valve, a standard gas reservoir, and a standard gas valve. All of the foregoing are operated automatically in such that start cycles, detector cycles, fault detection cycles, standardizing, analysis, shutdown and end cycles are performed in a way which allows straightforward and simple measurement of breath sample by a user.

14 Claims, 39 Drawing Sheets

FIG. 4
(A)
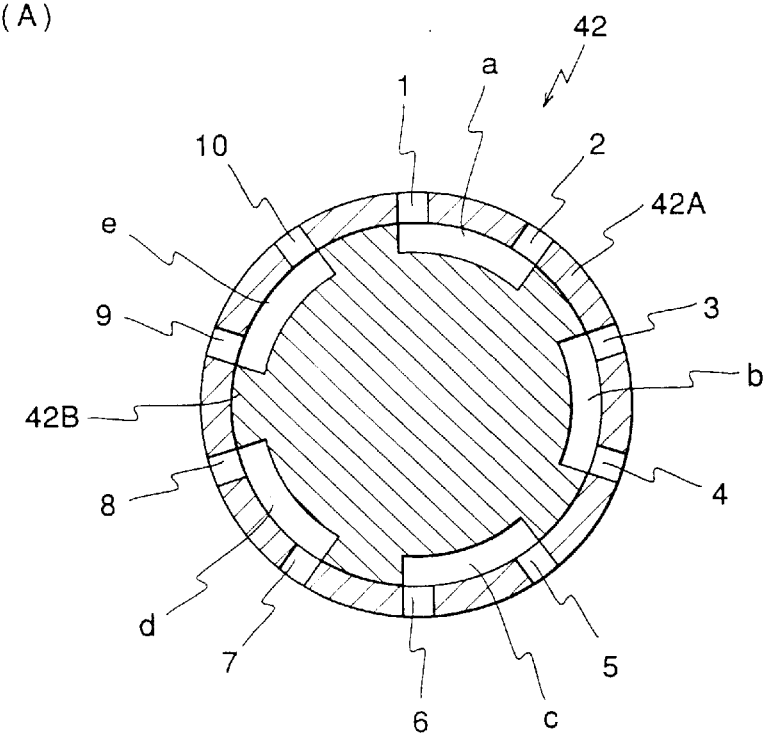
(B)
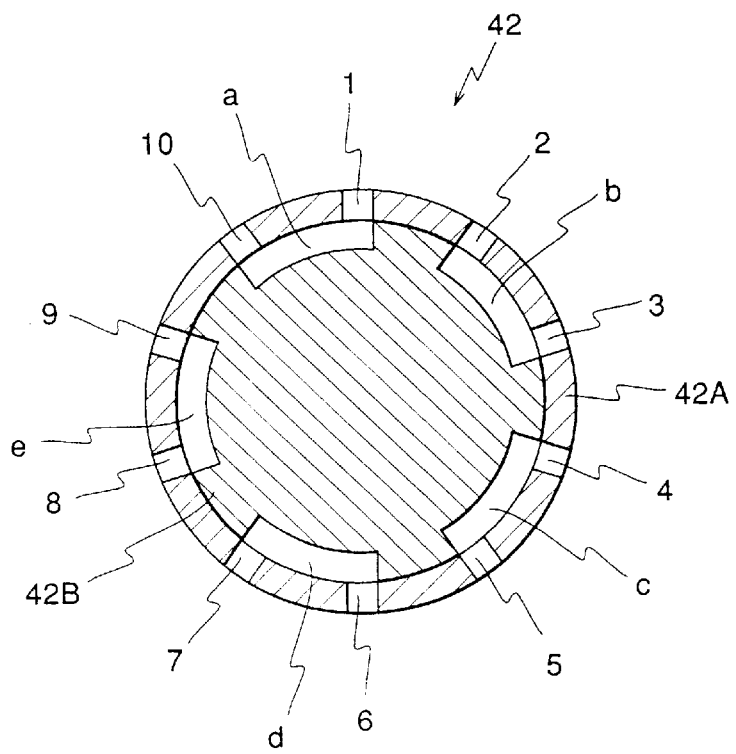

F I G. 8
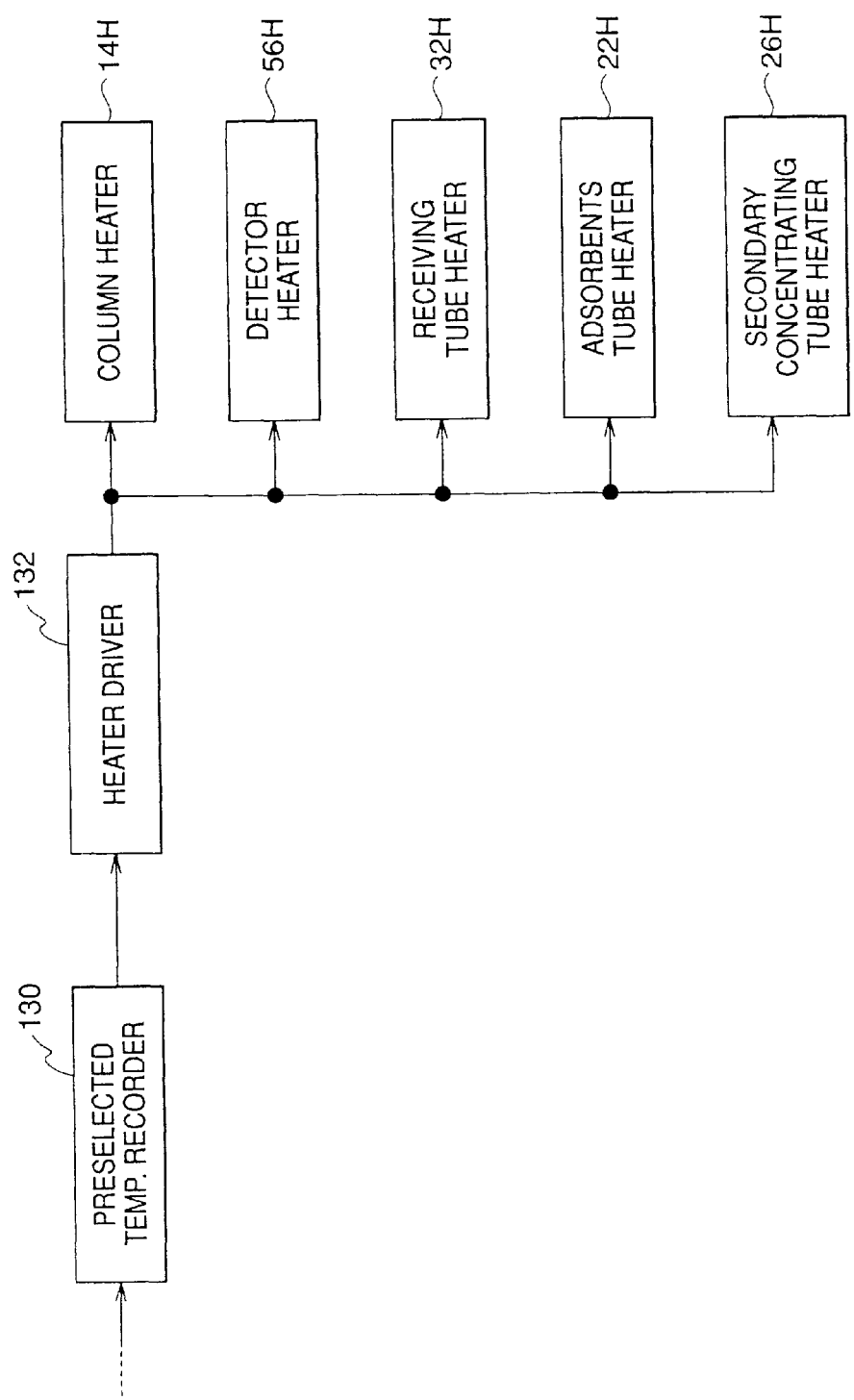

F I G. 1 9
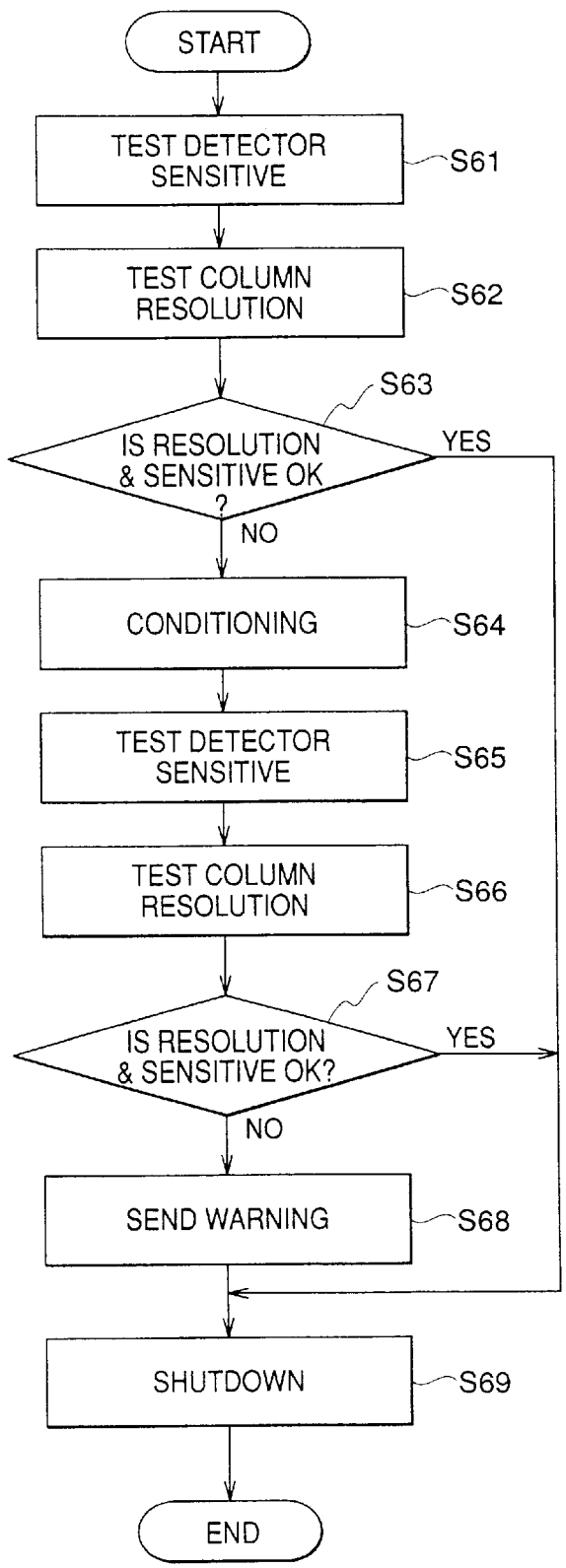

F I G. 2 4
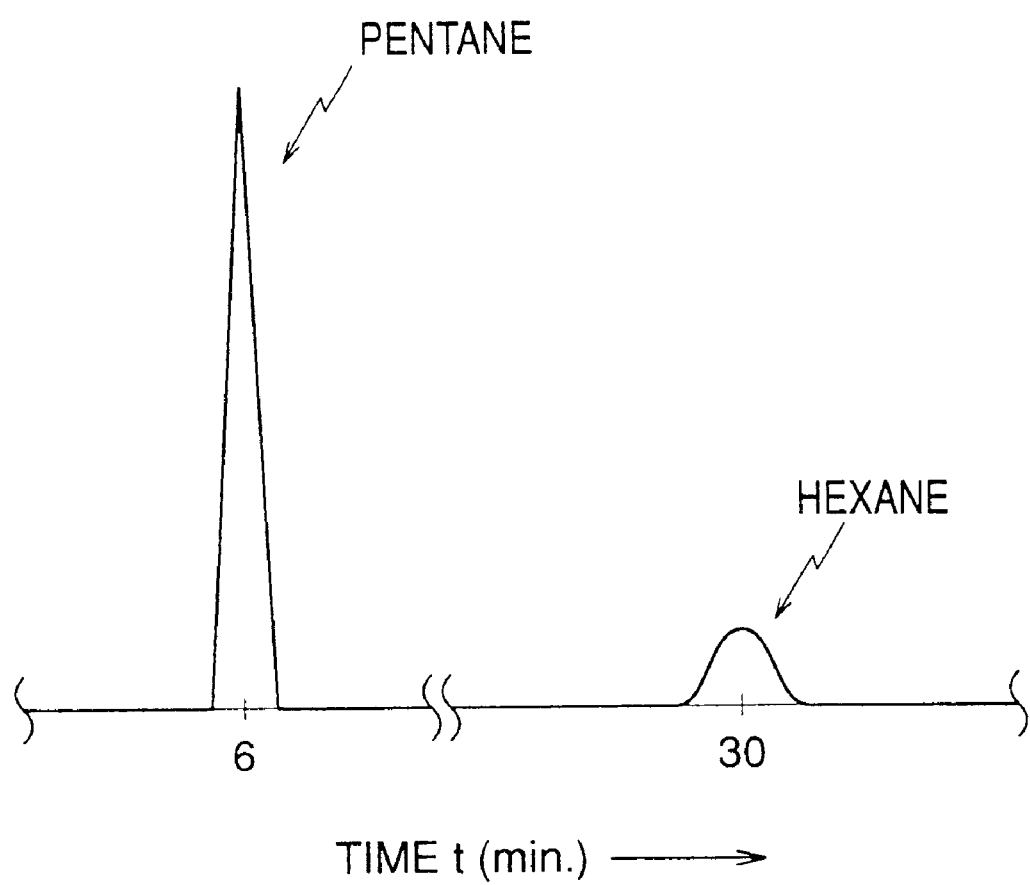

F I G. 2 5
(A)
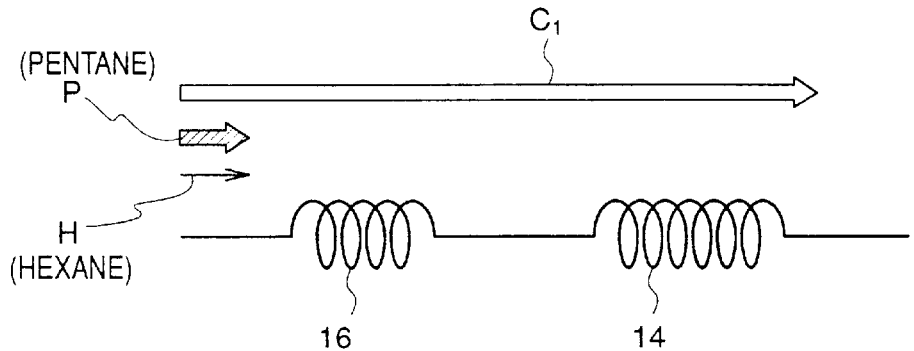
(B)
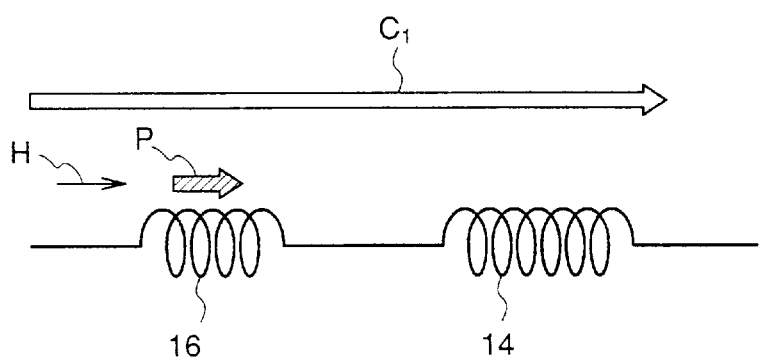
(C)
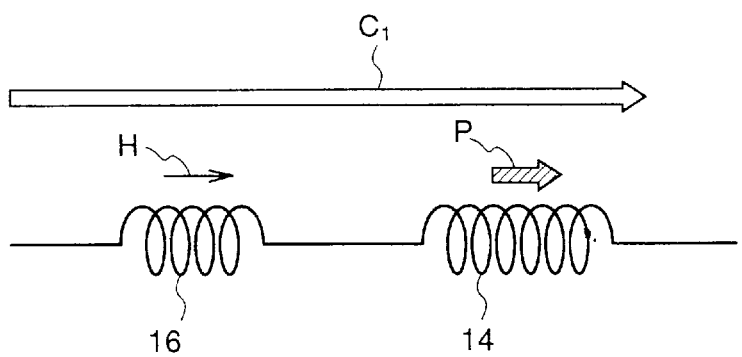
(D)
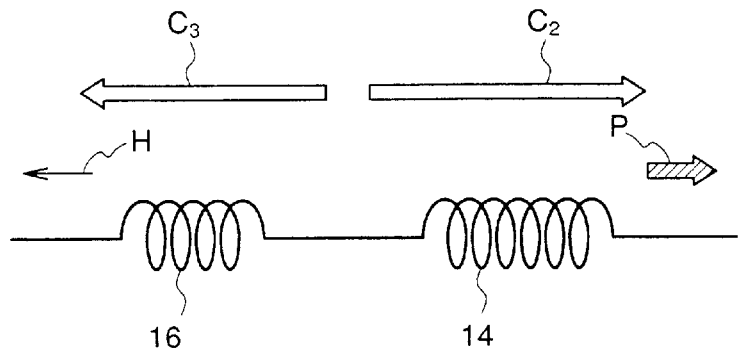

FIG.28
(A)
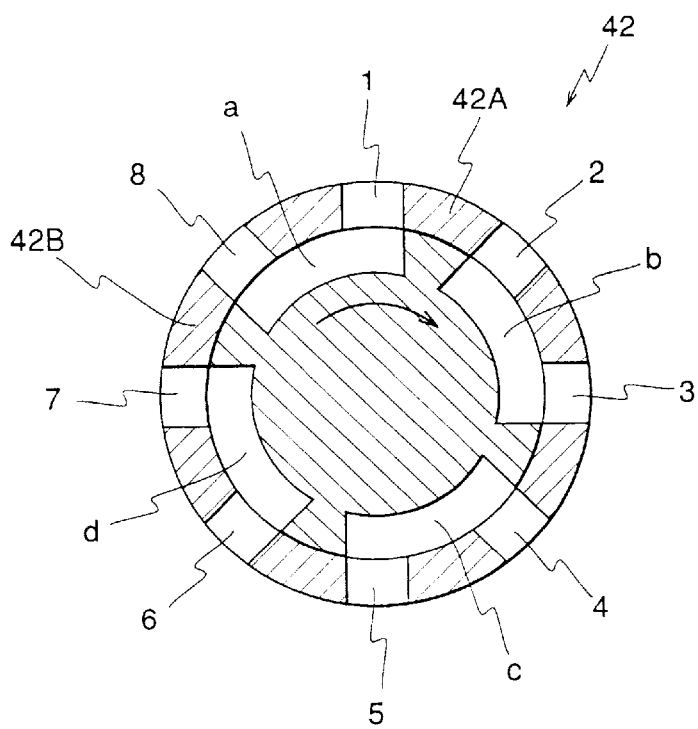
(B)
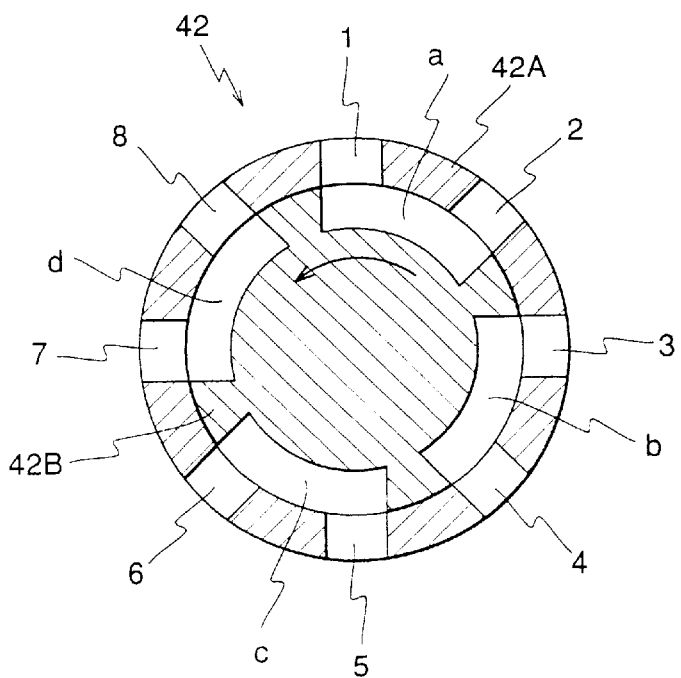

FIG.29
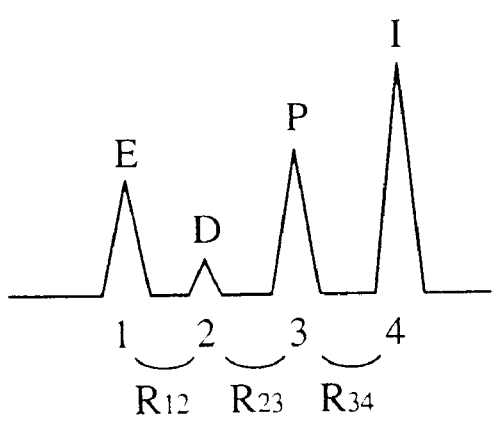
(a)
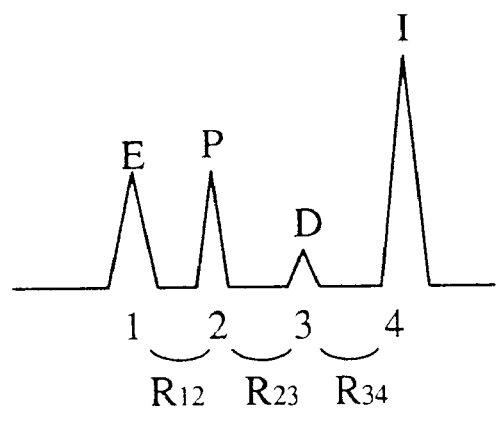
(b)

F I G. 3 6
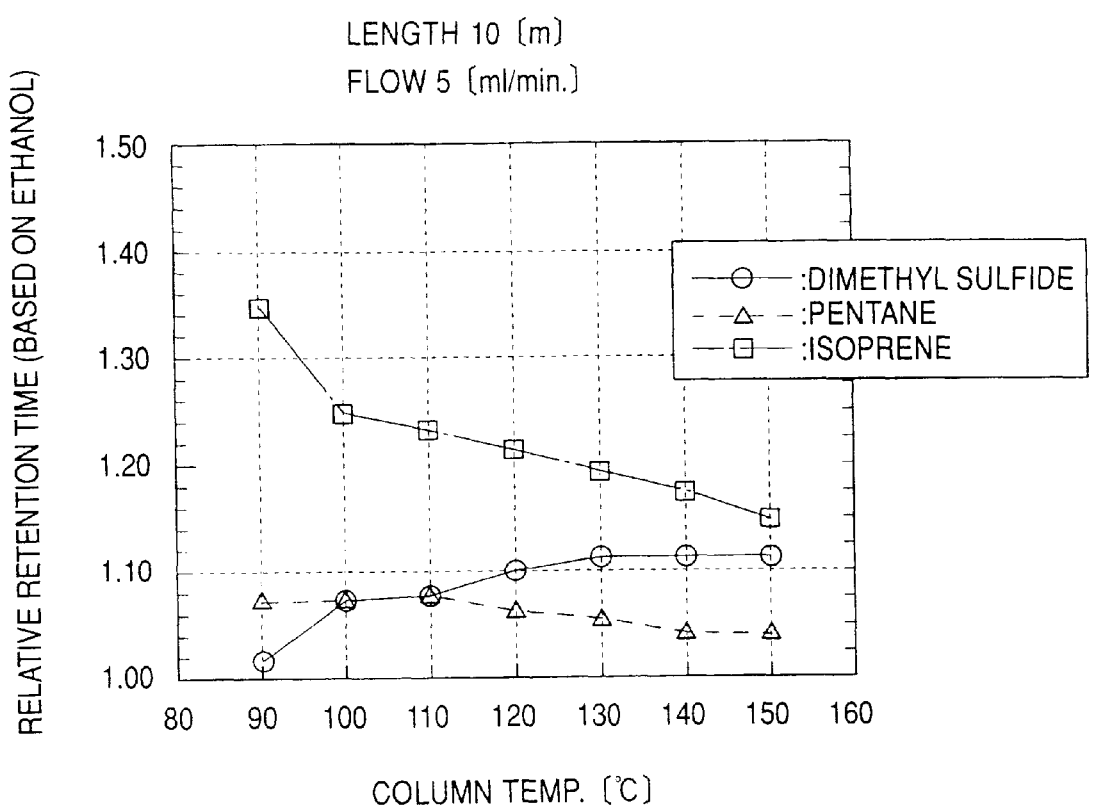

F I G. 3 7
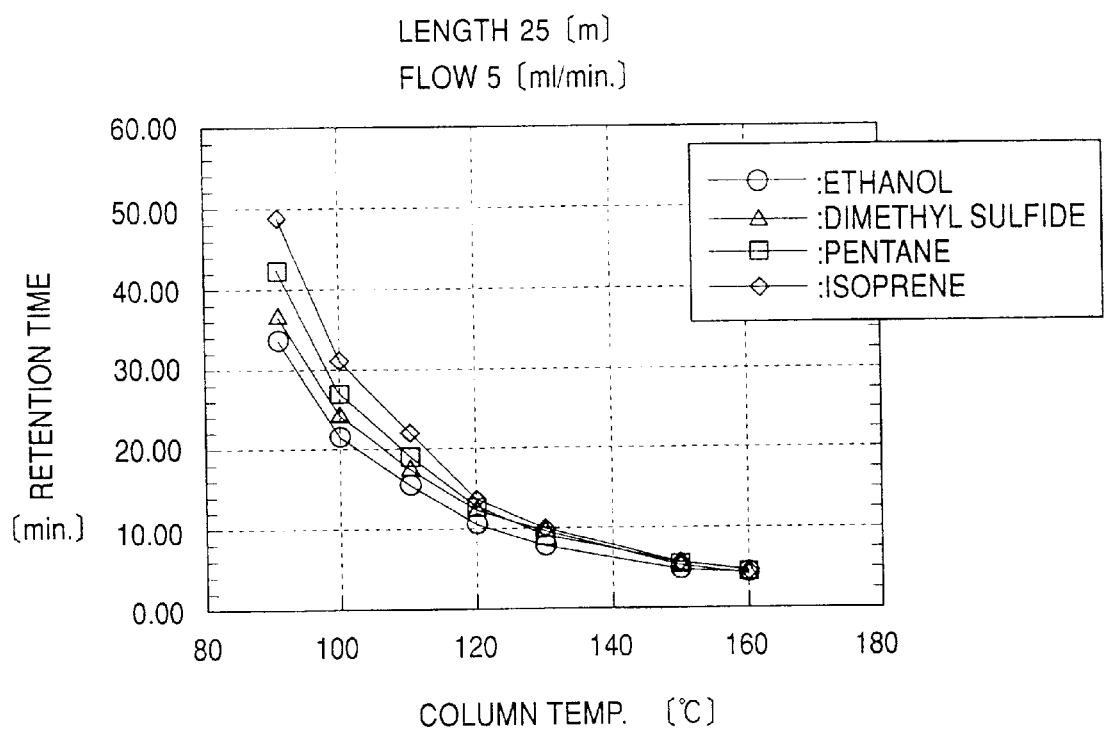
F I G. 3 8
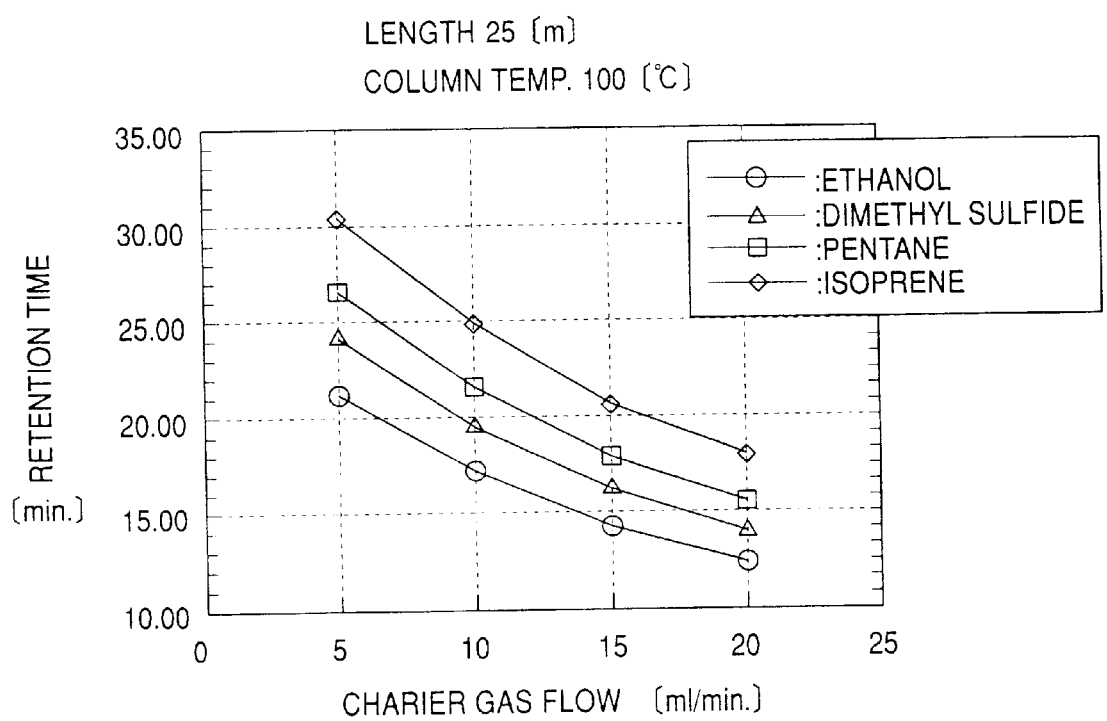

F I G. 3 9
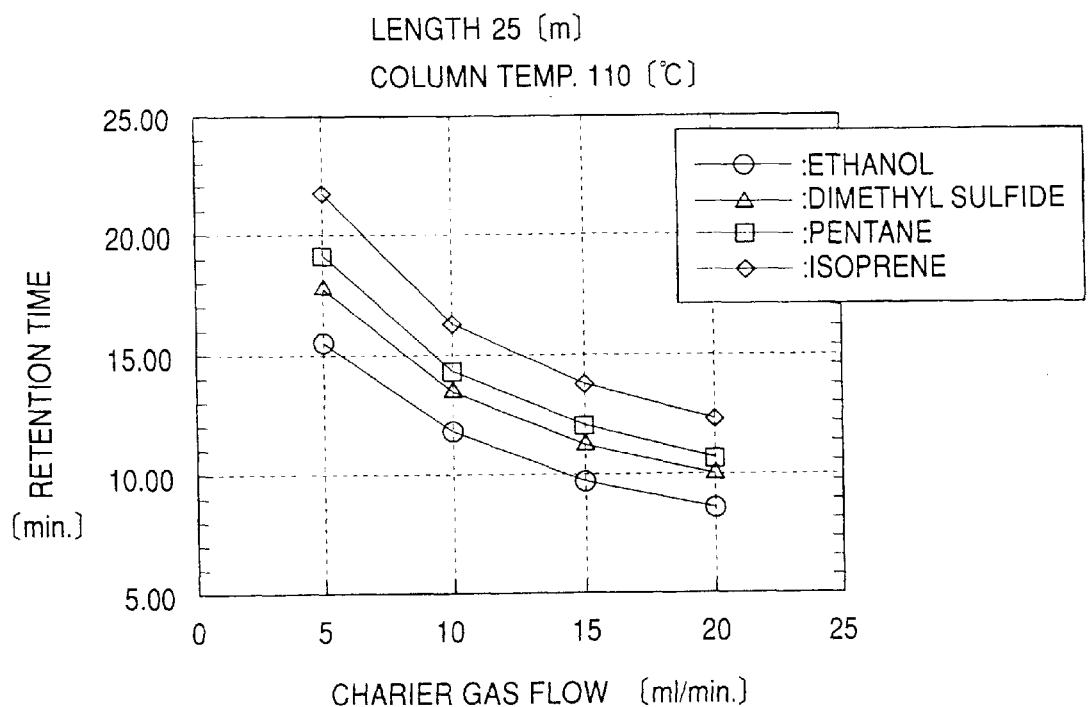
F I G. 4 0
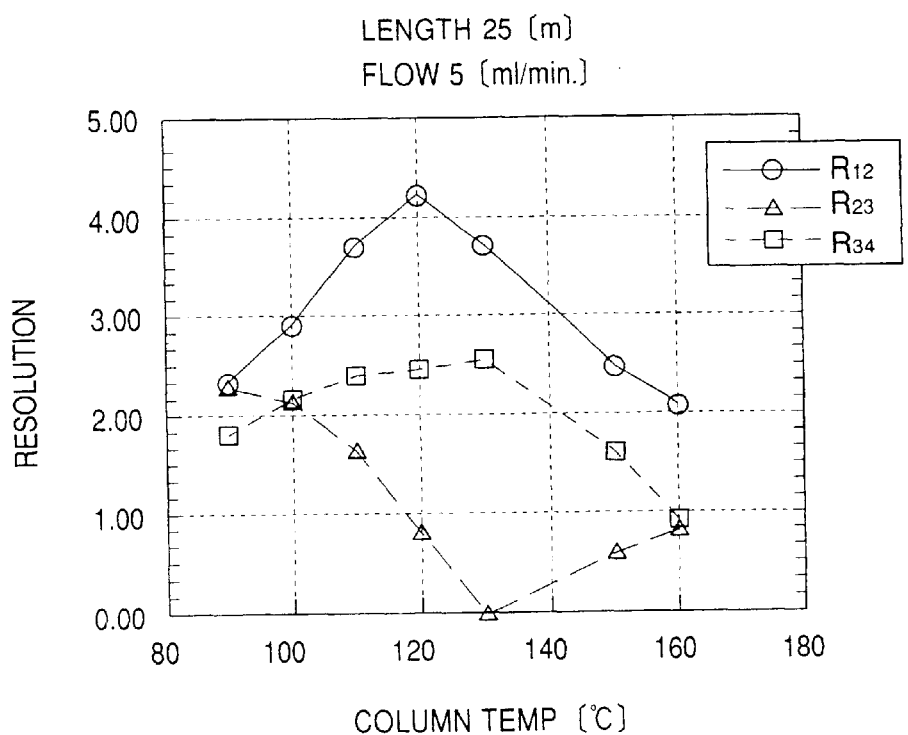

F I G. 4 3
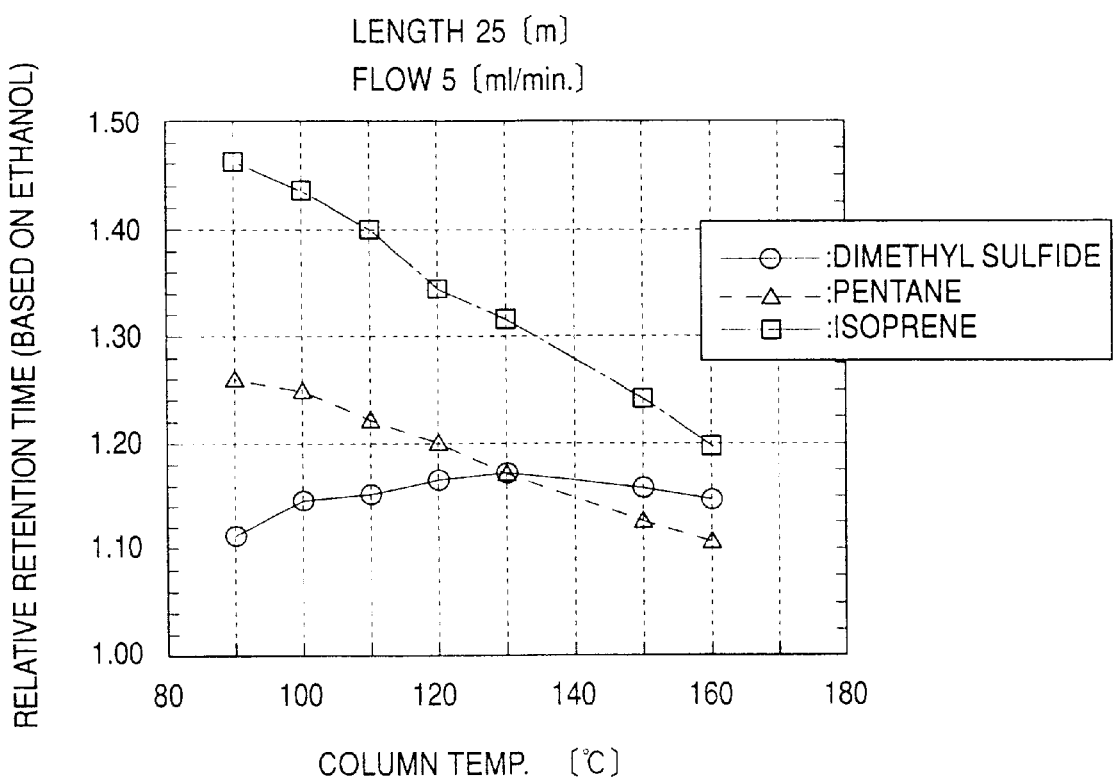

F I G. 4 4
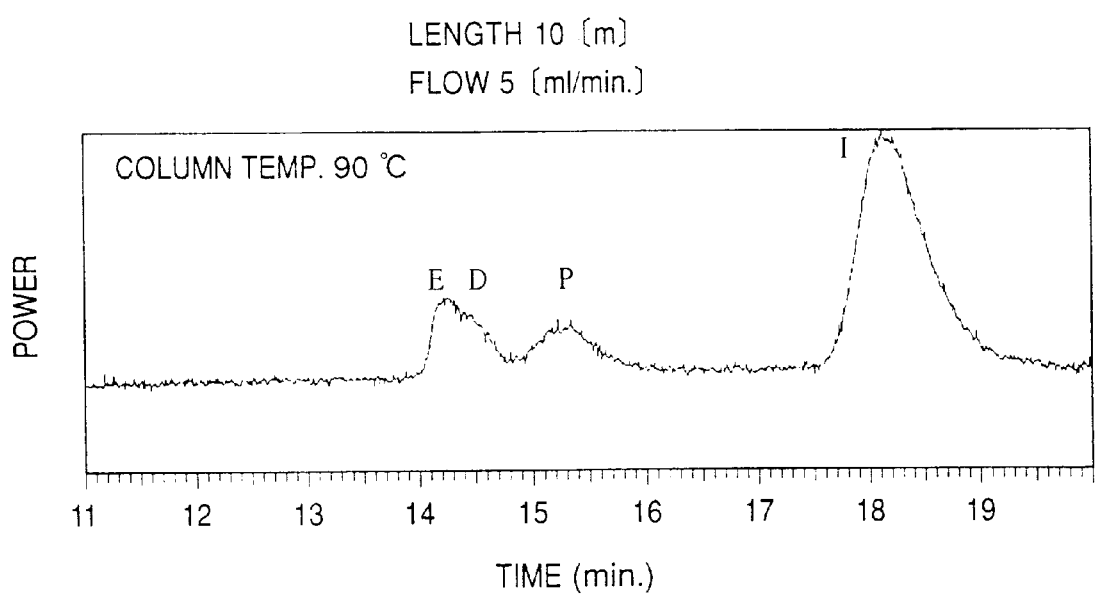
F I G. 4 5
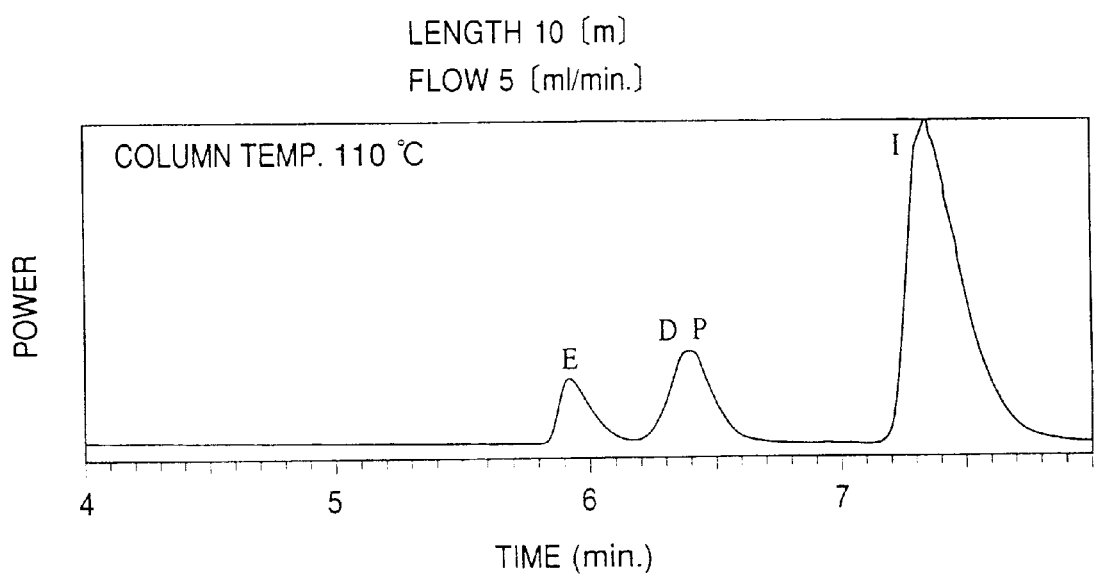

F I G. 4 6
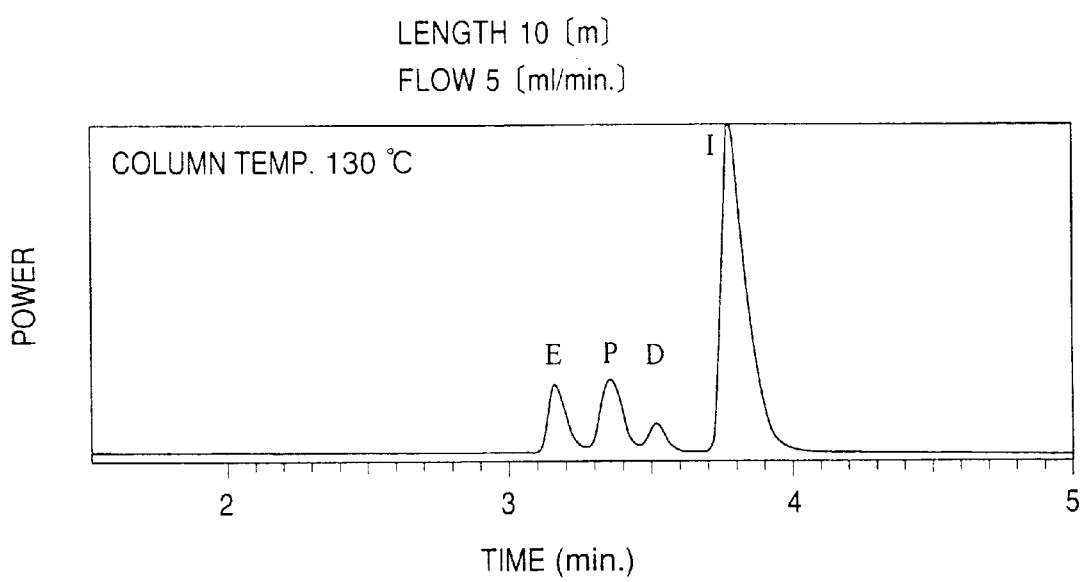
F I G. 4 7
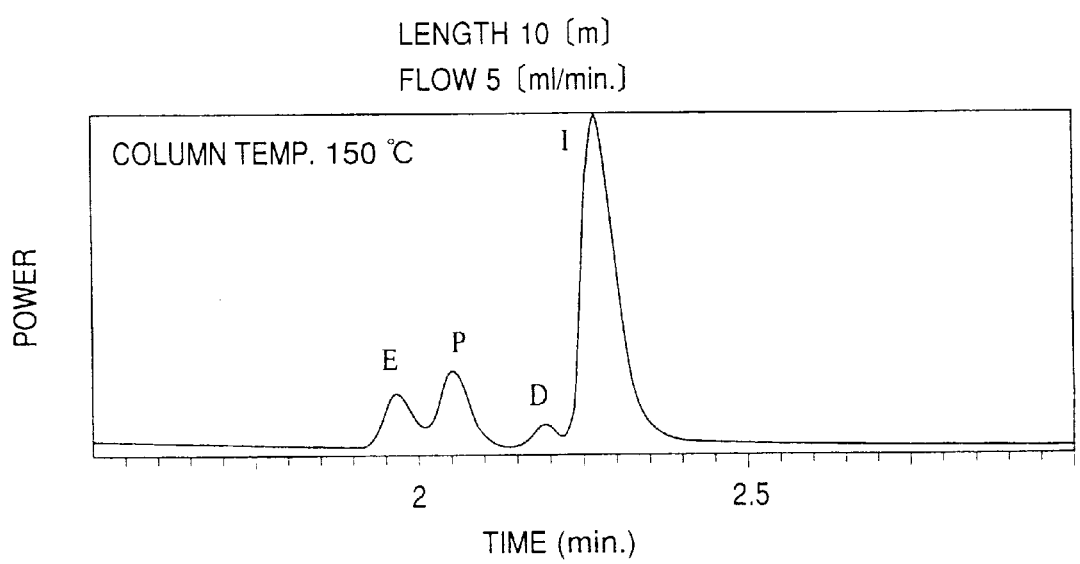

METHOD AND APPARATUS FOR ANALYZING BREATH SAMPLE

RELATED APPLICATION

This application is a divisional of application Ser. No. 08/910,113, Aug. 13, 1997, allowed now U.S. Pat. No. 6,148,657 granted Nov. 21, 2000.

FIELD OF THE INVENTION

The present invention relates to a method and an apparatus for analyzing constituents contained in a breath sample by means of gas chromatograph.

DESCRIPTION OF THE RELATED ART

There is conventionally available an apparatus for analyzing a breath sample based on detection of alcohol. On the other hand, analysis of constituents of a sample by the use of a gas chromatograph is popularly applied. The conventional chromatograph is used by researchers or engineers well versed in handling of the equipment. There is available no apparatus for automatically starting a gas chromatograph, analyzing and testing a sample, and then completing. For many of the users, therefore, the conventional chromatographic analysis apparatus is hard to use.

There is known no apparatus serving for clinical tests in the medical area by analyzing breath constituents. A breath analyzing apparatus for such medical tests should preferably be easily and automatically used by a test operator.

SUMMARY OF THE INVENTION

The present invention has an object to provide breath analyzing apparatus and method for analyzing a breath sample by means of a gas chromatographic column.

Another object of the invention is to provide breath analyzing apparatus and method which permit automatic and easy breath analysis of a low-concentration constituent such as pentane.

Further, another object of the invention is to provide breath analyzing apparatus and method which permit analysis of low-concentration constituents and high-concentration constituents by the use of a single main column and a detector.

Further, another object of the invention is to provide breath analyzing method and apparatus which permit perfect automation of start processing until the analyzing apparatus is ready to analyze.

Further, another object of the invention is to provide breath analyzing method and apparatus which permit perfect automation of shutdown processing upon completion of analysis and until supply of a carrier gas is discontinued.

Further, another object of the invention is to provide breath analyzing method and apparatus which permit automatic testing of deterioration of the column.

Furthermore, the present invention has an object to provide a breath analyzing method and a compact apparatus for the application thereof, which permit automation of various steps, completion of analysis in a shorter period of time of analysis and is easy to use in the area of clinical testing having needs different from those of laboratories.

Another object of the invention is to provide breath analyzing apparatus and method for carrying out measurement of a room interior environment, detection of a narcotic drug in vivo, and investigation of a cause of fire.

To achieve these objects of the invention, the apparatus of the invention comprises desorbing means for desorbing a breath sample absorbed into an absorbent sample tube, a chromatographic precolumn for passing the breath sample desorbed from the absorbent sample tube in a retention time prescribed for each constituent, a chromatographic main column for passing the breath sample having passed through the precolumn, in a retention time prescribed for each constituent, a detector for detecting constituents having passed through the main column, and a data processor for generating a chromatograph for the constituents detected by the detector. As a result of presence of the precolumn, when there are two constituents having different retention times, there remains, after passage of one constituent, for example pentane, through the main column, the other constituent such as hexane in the precolumn, thus permitting earlier completion of analysis by purging the main column and the precolumn. Presence of the desorbing means permits satisfactory detection of low-concentration constituents contained in the breath such as pentane, dimethyl sulfide and isoprene.

Further, the apparatus of the invention comprises a sample receiving tube for receiving the exhaled breath sample, a sample loop for aspirating a prescribed quantity of breath sample from the sample receiving tube, and a sample valve which connects the sample loop and the main column when a breath sample is aspirated into the sample loop. This makes it possible to sample a high-concentration constituent in the breath such as acetone directly from the sample receiving tube and analyze the sampled constituent by means of the main column.

The apparatus of the invention further comprises a standard gas bottle for supplying a standard gas, and a standard gas valve which connects the standard gas bottle and the sample loop when testing sensitivity of said-column. This permits automatic testing of the column.

In a preferred embodiment, the apparatus of the invention comprises an interface having various buttons and a controller controlling start, analysis, testing and shutdown of the apparatus in response to an instruction to the interface.

In another preferred embodiment, there is disclosed a method necessary for separating isoprene and pentane by the use of the foregoing apparatus.

BRIEF DESCRIPTION OF THE DRAWINGS

FIGS. 4(A) and 4(B) are schematic sectional views of the sampling valve;

FIG. 8 is a block diagram illustrating the configuration of temperature control means;

FIG. 19 is a flowchart illustrating an example of test processing;

FIG. 24 is a chromatograph illustrating retention times for pentane and hexane;

FIGS. 25(A)–25(D) are descriptive views illustrating examples of backlash;

FIGS. 28(A) and 28(B) are schematic sectional views of the sampling valve;

FIGS. 29(A) and 29(B) are chromatographs for illustrating resolutions R12, R23 and R34;

FIG. 36 is a graph illustrating relative retention times for the individual constituents relative to capillary column temperature in a capillary column having a length of 10 [m] with a carrier gas flow rate kept constant at 5 [ml/min.];

FIG. 37 is a graph illustrating retention times for the individual constituents relative to capillary column temperature in a capillary column haviang a length of 25 [m] with a carrier gas flow rate kept constant at 5 [ml/min.];

FIG. 38 is a graph illustrating retention times for the individual constituents relative to carrier gas flow rate in a capillary column having a length of 25 [m] with a capillary column temperature kept constant at 100° C.;

FIG. 39 is a graph illustrating retention times for the individual constituents relative to carrier gas flow rate in a capillary column having a length of 25 [m] with a capillary column temperature kept constant at 110° C.;

FIG. 40 is a graph illustrating resolutions for the individual constituents relative to capillary column temperature in a capillary column haviang a length of 25 [m] with a carrier gas flow rates kept constant at 5 [ml/min.] ;

FIG. 43 is a graph illustrating relative retention times for the individual constituents relative to capillary column temperature in a capillary column having a length of 25 [m] with a carrier gas flow rate kept constant at 5 [ml/min.] .

FIG. 44 is a chromatograph in a capillary column having a length of 10 [m] with a carrier gas flow rate kept constant at 5 [ml/min.] and a capillary column temperature kept constant at 90° C.;

FIG. 45 is a chromatograph in a capillary column having a length of 10 [m] with a carrier gas flow rate kept constant at 5 [ml/min.] and a capillary column temperature kept constant at 110° C.;

FIG. 46 is a chromatograph in a capillary column having a length of 10 [m] with a carrier gas flow rate kept constant at 5 [ml/min.] and a capillary column temperature kept constant at 130° C.;

FIG. 47 is a chromatograph in a capillary column having a length of 10 [m] with a carrier gas flow rate kept constant at 5 [ml/min.] and a capillary column temperature kept constant at 150° C.;

DETAILED DESCRIPTION OF THE PREFERRED EMBODIMENTS

Overview

Figure 1:
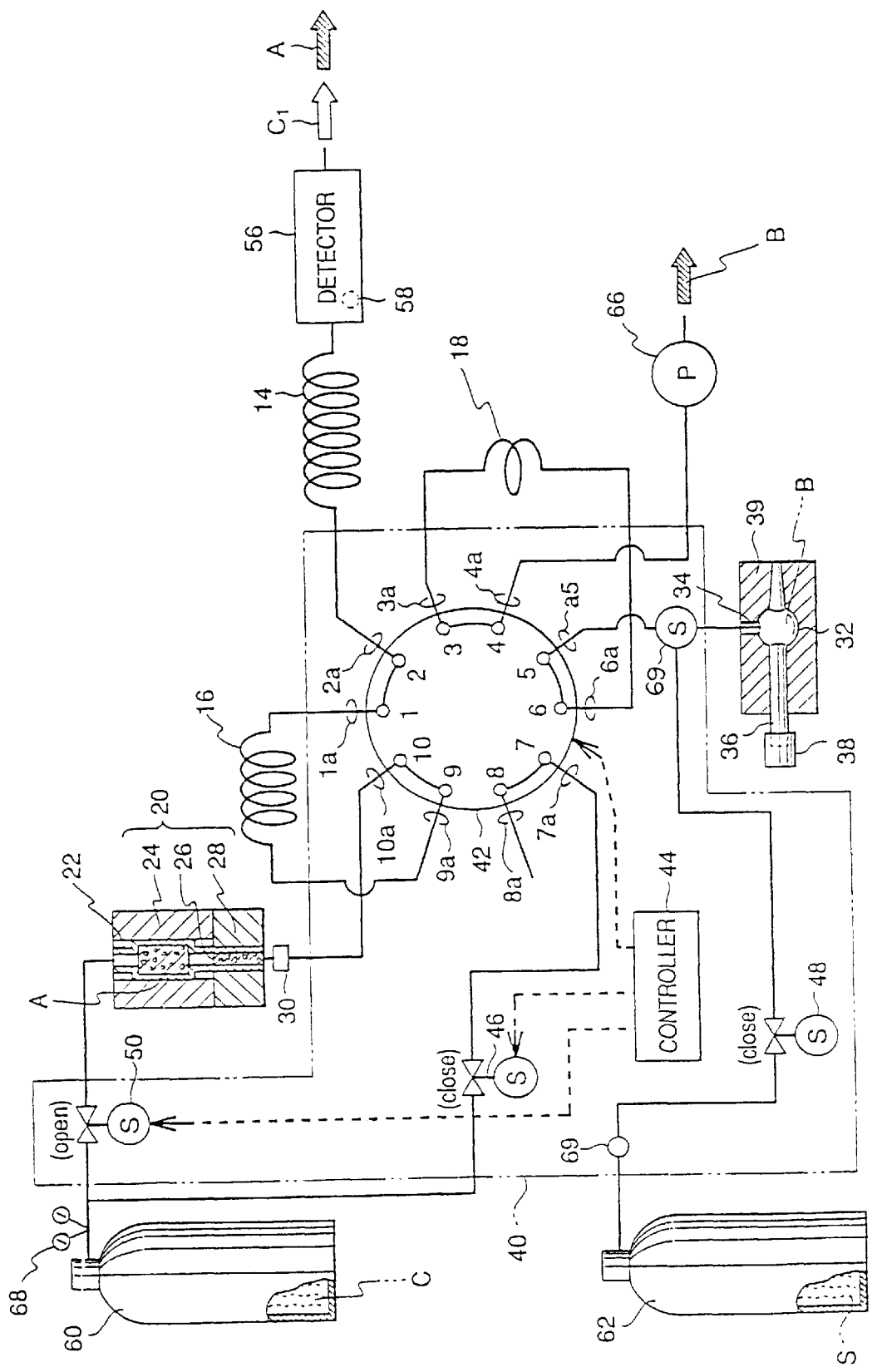
FIG. 1 is a configurational view of an embodiment of the present invention.

Referring to FIG. 1, the breath analyzing apparatus 12 of the invention comprises a main column 14 and a precolumn 16 for passing a breath sample A therethrough and separating constituents contained in the breath sample A, and a detector 56 for detecting the constituents separated by the precolumn 16 and the main column 14. The detector 56 may be any of ones detecting mass, thermal conductivity, and ion current.

The apparatus 12 further comprises an absorbent sample tube 22 absorbing the breath sample A in the interior thereof, and desorbing means 20 desorbing the breath sample A absorbed in the absorbent sample tube 22. Low-concentration constituents contained in the breath sample are introduced from the desorbing means into the column. The apparatus 12 is further provided with a sample receiving tube 32 receiving a breath B breathed out by a subject, a sample loop 18 aspirating the breath B in a certain quantity, and a pump 66 aspirating the breath B in the sample receiving tube 32 though the sample loop 18. High-concentration constituents of the breath sample are introduced from the sample receiving tube and the sample loop into the column 14.

The apparatus 12 further comprises a standard gas bottle 62. The standard gas bottle 62 is filled with a standard gas S comprising known constituents. The standard gas is a mixture of, for example, helium with isoprene and pentane. Isoprene and pentane should have the same concentrations as in desorbing the breath sample at the desorbing means 20*f*. Standard gas storing means 69 is a storage vessel for storing the standard gas in a certain quantity (for example, 500 ml) to ensure smooth supply of the standard gas S. Bringing the standard gas into contact with the breath analyzing apparatus is useful for testing resolution of the column or for confirming the retention time.

The breath analyzing apparatus of the invention further comprises channel switching means 40. The channel switching means 40 has a sample valve 42, a standard gas valve 43, solenoid valves 46, 48 and 50, and a controller for switching over the individual solenoid valves 46, 48 and 50 and the individual valves 42 and 43. The controller 44 may be one comprising manual switches, one comprising relays and timers, or one comprising a microcomputer and programs thereof. A carrier gas bottle 60 filled with a carrier gas C is connected through a reducing valve 68 to the channel switching means 40. Air, hydrogen, nitrogen, helium or argon is usually used as a carrier gas C.

Figure 2:
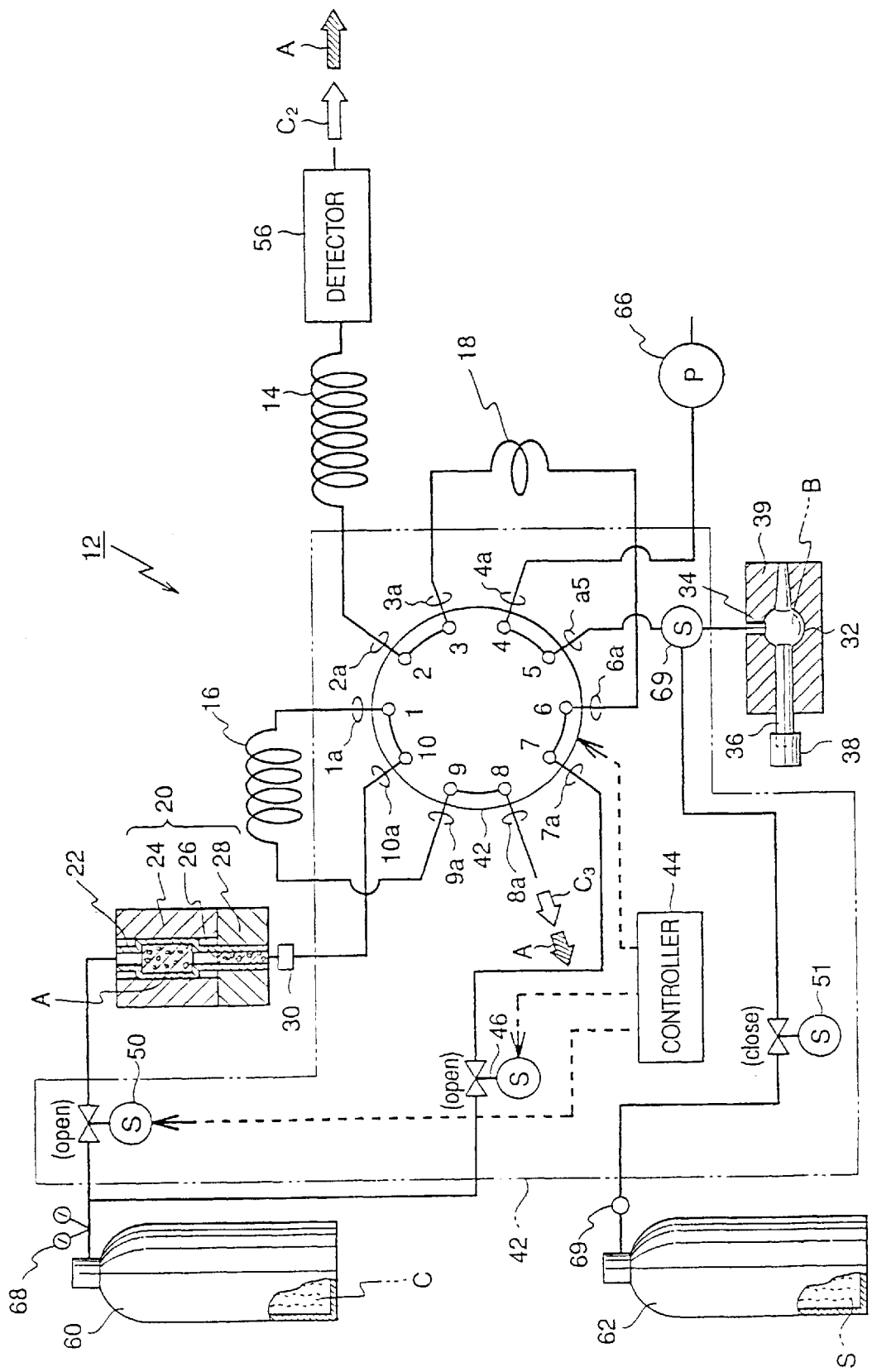
FIG. 2 is the same view as FIG. 1 in which the sample valve is changed.

The sample valve 42 selects any one of the desorbing means 20 and the sample receiving tube 32. The sample valve has a plurality of ports serving as outlets, ten ports in the example shown in FIG. 1. The sample valve has two operating positions: FIG. 1 shows the first operating position and FIG. 2 shows the second operating position. In FIG. 1, the port 1 is connected to the port 2, the port 3 is connected to the port 4, and similarly all the ports up to the port 10 are sequentially connected. In FIG. 2, on the other hand, the port 2 is connected to the port 3, the port 4 is connected to the port 5, and all the ports are sequentially connected by shifting by one from the first operating position.

The standard gas valve 43 comprises an inlet connected to the sample receiving tube 32, an inlet connected to the standard gas bottle 62, an outlet connected to the sample valve 42, and a line connecting any one of the inlets to the outlet by switching.

The desorbing means 20 comprises an absorbent sample tube support 24 supporting the absorbent sample tube 22, a secondary concentrating tube 26 absorbing the breath sample A in the interior thereof, and a secondary concentrating tube support 28 supporting the secondary concentrating tube 26. The absorbent sample tube support 24 has a built-in absorbent sample tube heater, described further in connection with FIG. 5 for desorbing the breath sample A absorbed in the absorbent sample tube 22. The secondary concentrating tube support 28 has a secondary concentrating tube cooler 26H for absorbing the breath sample A desorbed from the absorbent sample tube 22 into the secondary concentrating tube 26, and a secondary concentrating tube heater, described further in connection with FIG. 5, for desorbing the breath sample A absorbed in the secondary concentrating tube 26 by heating the secondary concentrating tube 26. The heater is for example an electric heater, and the cooler performs cooling by the use of liquid nitrogen for example.

A capillary tube having an inside diameter within a range of from 0.5 to 1.0 mm is used as the secondary concentrating tube 26. The material should preferably be the same as, or equivalent in properties with, that of the main column 14. The secondary concentrating tube 26 should be coated with a liquid absorbent to improve efficiency of secondary concentration.

The sample receiving tube 32 has a breath discharging port 34 and a breath blowing port 36. The subject attaches a disposable mouth piece 38 to the breath blowing port 36, presses the mouth piece 38 against his or her mouth, and blows a breath B into the sample receiving tube 32. The sample receiving tube support 39 supports the sample receiving tube 32, and has a receiving tube heater for heating the breath B or the like.

Referring again to FIG. 1, the breath analyzing apparatus 12 has a breath sucking line for sucking a breath breathed out by the subject through the ports 5 and 6 into the sample loop, to analyze the breath breathed out by the subject.

Referring to FIG. 2, the apparatus 12 has a first carrier gas line carrying the breath sucked into the sample loop to the sample valve 42, the main column 14, and the detector 56 by means of a pump. When the solenoid valve 46 is open, the first carrier gas line sends the carrier gas through the ports 7 and 6 to the sample loop, and sends the blown out breath through the ports 3 and 2 to the main column.

As shown in FIG. 1, the apparatus 12 has a second carrier gas line for carrying the breath sample desorbed from the absorbent sample tube 22 to the sample valve 42, the precolumn 16, the main column 14 and the detector 56, to analyze the breath sample concentrated in the absorbent sample tube 22. When the solenoid valve 50 is open, the carrier gas line sends the carrier gas from the desorbing means 20 to the ports 10 and 9, the precolumn 16, the ports 1 and 2 and the main column 14.

The first carrier gas line serves also as a third carrier gas line for carrying the standard gas sucked into the sample loop 18 to the sample valve 42, the main column 14 and the detector 56.

Referring to FIG. 2, the apparatus 12 is further provided with a fourth carrier gas line C2 which carries the constituents having passed through the precolumn 16 of the breath sample desorbed from the absorbent sample tube 22 to the sample valve 42, and the main column 14, and a fifth carrier gas line C3 which purges the constituents not having passed through the precolumn 16 of the breath desorbed from the absorbent sample tube 22 from the sample valve 42. When performing backflash, the second carrier gas line C1 shown in FIG. 1 is switched over to the fourth and the fifth carrier gas lines C2 and C3 shown in FIG. 2.

Figure 3:
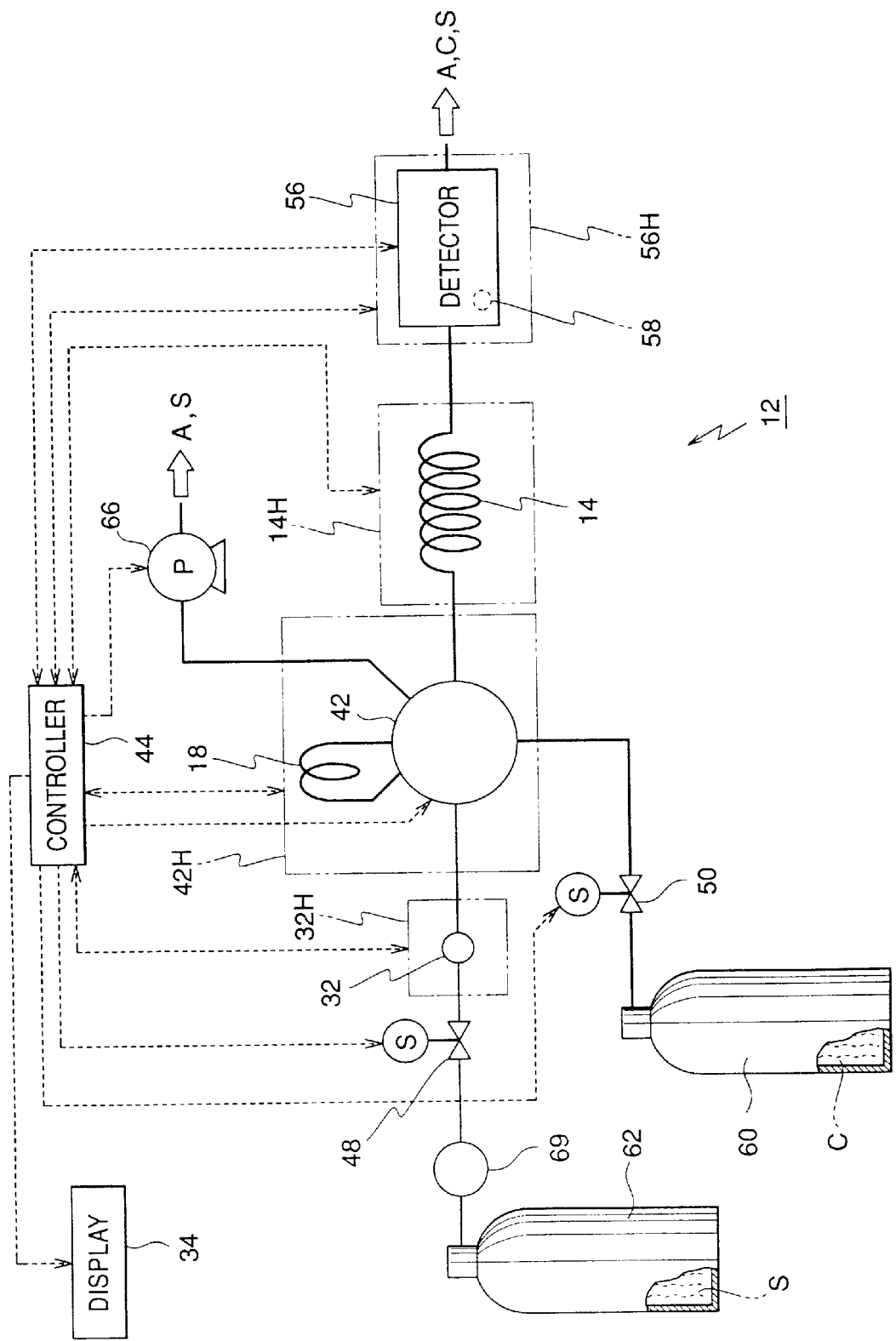
FIG. 3 illustrates the relationship between the controller and the individual heaters.

Referring to FIG. 3, the apparatus 12 is further provided with a column heater 14H heating the column 14, a detector heater 56H heating the detector 56, a sample receiving tube heater 32H heating the sample receiving tube 32, and a thermostatic oven 42H heating the sample loop 18 and the sample valve 42. The controller 44 controls temperature of the individual heaters. A display 34 for displaying the test result or the completion of start processing using the standard gas is connected to the foregoing controller 44.

Referring to FIG. 4, the sampling valve 42 is a rotary valve having ten ports 1 to 10. FIG. 4 is a schematic sectional view illustrating an example of sampling valve 42. In FIG. 4, the sampling valve 42 is composed of a fixed body 42A having ports 1 to 10, a rotating body 42B having communicating vessels a to e, and an actuator (not shown) such as a solenoid for rotating the rotating body 42B. FIG.

4(A) illustrates a first operating position shown in FIG. 1, and FIG. 4(B) illustrates a second operating position shown in FIG. 2.

Referring again to FIG. 1, a piping 1a connected to an end of the precolumn 16 is connected to the port 1. A piping 2a connected to an end of the main column 14 is connected to the port 2. A piping 3a connected to an end of the sample loop 18 is connected to the port 3. A piping 4a connected to the pump 66 is connected to the port 4. A piping 5a connected to the sample receiving tube 32 is connected to the port 5. A piping 6a connected to the other end of the sample loop 18 is connected to the port 6. A piping 7a for introducing the carrier gas C2 through the solenoid valve 46 is connected to the port 7. A piping 8a (vent) for discharging the carrier gas C3 having passed through the desorbing means 20 and the precolumn 16 is connected to the port 8. A piping 9a connected to the other end of the precolumn 16 is connected to the port 9. A piping 10a introducing the carrier gas C1 and C3 having passed through the desorbing means via a filter 20 is connected to the port 10.

Figure 5:
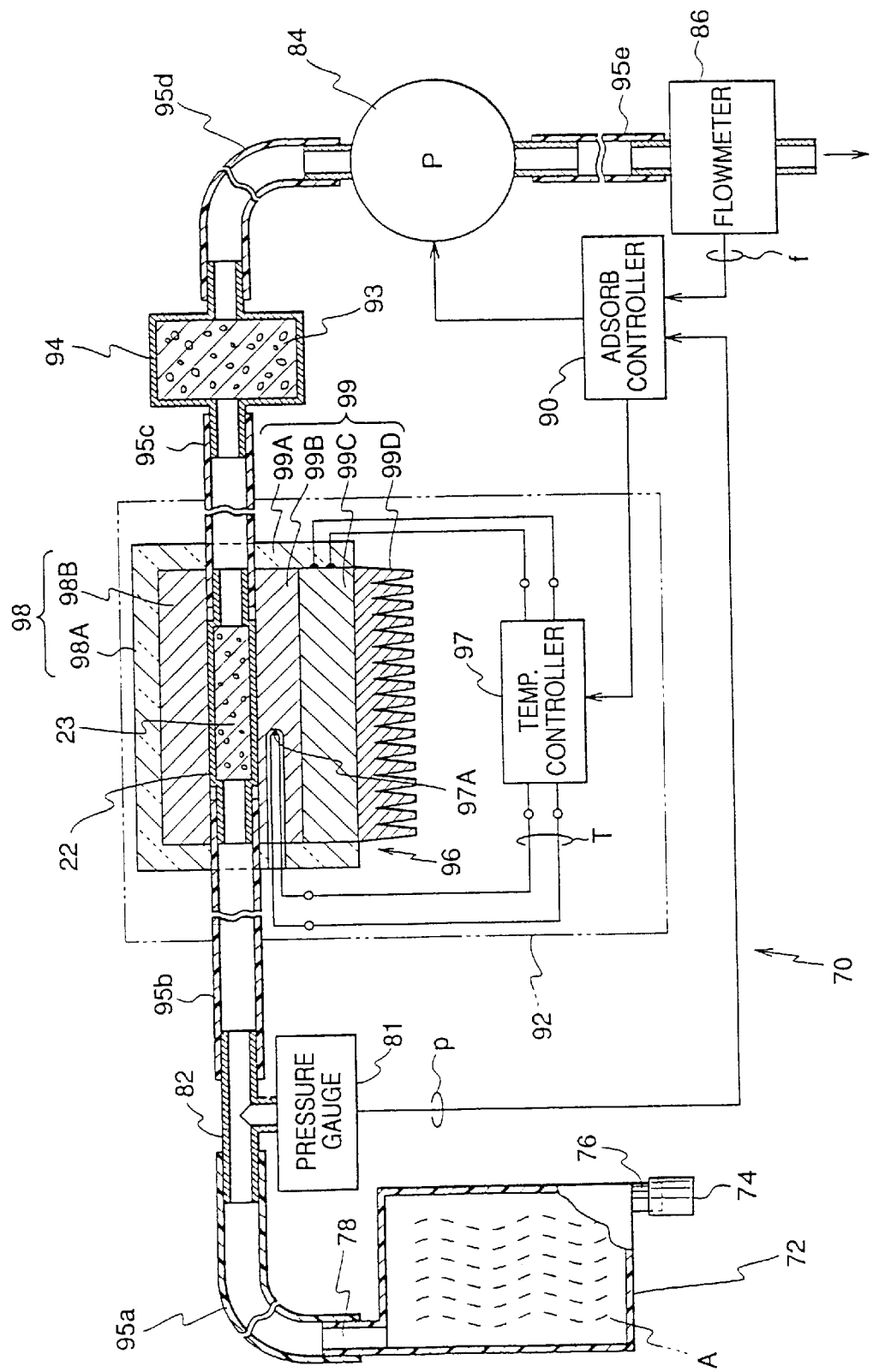
FIG. 5 is a configurational view of absorbing means.

Referring to FIG. 5, the breath concentrating/absorbing unit 80 for absorbing the breath sample A into the absorbent sample tube 22 comprises a Teddler bag 72 filled with breath A, the absorbent sample tube 22 connected to the Teddler bag 72, and a pump 84 for sucking the breath A in the Teddler bag 72 into the absorbent sample tube 22.

Further, the breath concentrating/absorbing unit 80 is provided with a mass flowmeter 86 for measuring a mass flow rate f of the breath A passing through the absorbent sample tube 22, a manometer 81 for measuring pressure p of the breath A in the Teddler bag 72, an absorption control means 90 for stopping the pump 84 when pressure p of the breath A measured by the manometer 81 is under a prescribed value pF, a thermostat 92 for keeping a constant temperature T of the absorbent sample tube 22, and a water absorbing filter 94 provided in the channel of the breath A between the absorbent sample tube 22 and the pump 84.

The Teddler bag 72, a tee 881 of the manometer 81, the absorbent sample tube 22, the water absorbing filter 94, the pump 84 and the mass flowmeter 86 are individually connected by flexible tubes 95a to 95e.

The absorbent tube 22 has an absorbent 23 for absorbing the breath sample A. The Teddler bag 72 has a breath inlet port 74 and a breath discharging port 78. A stop valve capable of being manually opened and closed is provided for each of the breath discharging port 78 and the breath inlet port 76. The subject previously attaches the disposable mouth piece 74 to the breath inlet port 76, presses his or her mouth against the mouth piece 74, and blows breath A into the Teddler bag 82. The mass flowmeter 86 is a common flowmeter for gas such as a mass flowmeter. The manometer 81 utilizes the piezo-electric effect in which voltage is generated by applying a pressure onto a piezo-electric element.

According to the result of an experiment, pressure p during sucking is, for example, $-0.05$ kgf/cm$^2$, and pressure p upon completion of sucking is, for example, within a range of from $-0.3$ to $-0.4$ kgf/cm$^2$. To determine the completion of sucking, pressure is measured with the manometer 81. The thermostat 92 is composed of a heating/cooling unit 96 and a temperature control unit 97. The heating/cooling unit 96 can be divided into an upper portion 98 and a lower portion 99, and the upper portion 98 and the lower portion 99 hold the absorbent sample tube 22 in between. The upper portion 98 has a heat insulating member 98A and a heat conducting member 98B. The lower portion 99 has a heat insulating member 99A, a heat conducting member 99B, a Peltier element 99C and a radiation fin 99D.

A thermocouple 97A is provided in the heat conducting member 992. The thermocouple 97A provides an output of voltage corresponding to temperature T of the absorbent sample tube 22 to the temperature control means 97. The temperature control means 97 controls feeding of power to the Peltier element 99C so that temperature T of the absorbent sample tube 22 as given by an output from the thermocouple 97A is constant at a certain value TC. When the certain value TC is over room temperature, a simple electric heater or the like may be provided in place of the Peltier element 99C. The water absorbing filter 94 is filled with a hygroscopic agent 93 such as silica gel or calcium carbide.

When the pump 84 is operated, the breath A is sucked from the Teddler bag 82 through the absorbent sample tube 22. As a result, the breath constituents A are concentrated and caught by the absorbent 141 of the absorbent sample tube 22. At this point, pressure p upon sucking is measured by the manometer 88, and mass flow rate is measured by the mass flowmeter 86. When the Teddler bag 82 becomes empty, pressure p reaches the level of a certain value pF, and the main control means 90 causes stoppage of the pump 84. The mass flow rate f upon completion of sucking is provided from the mass flowmeter 86 to the sucking control means 90. The sucking control means 90 therefore calculates the quantity of breath A concentrated in the absorbent sample tube 22.

Figure 6:
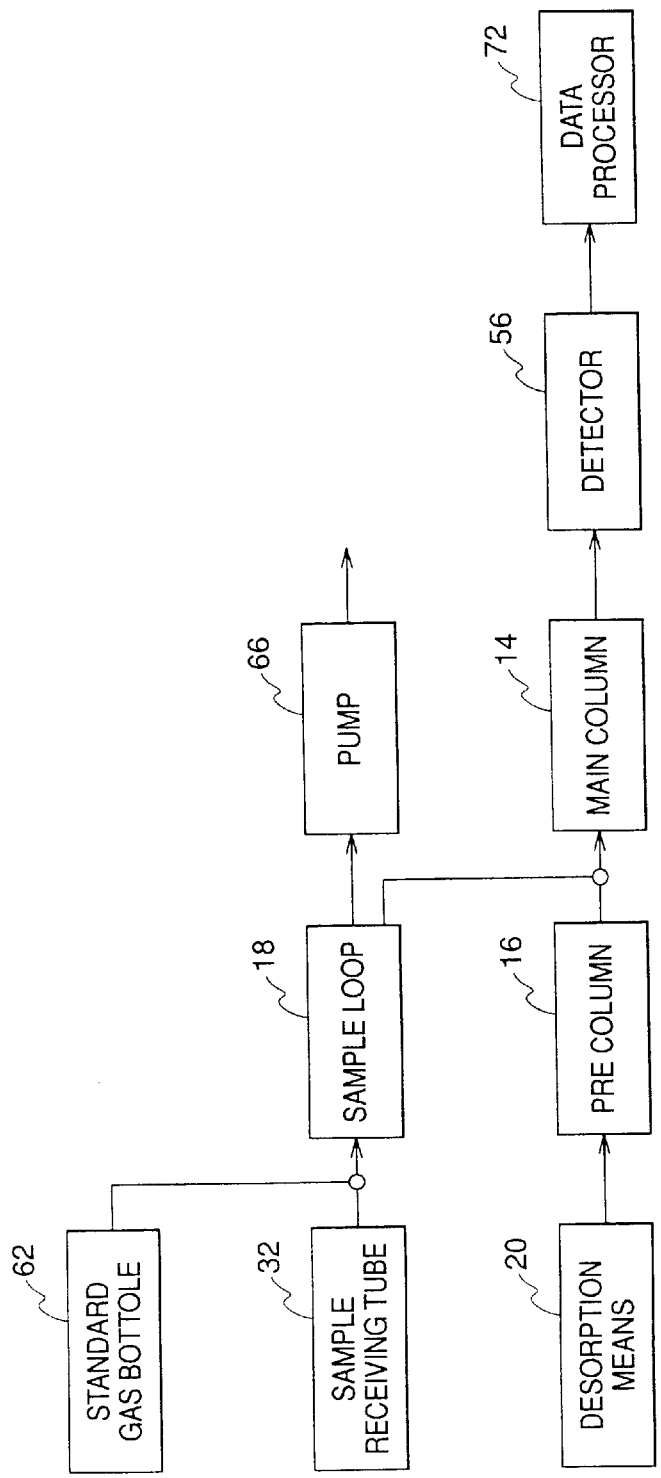
FIG. 6 is a block diagram illustrating the configuration of another embodiment of the invention.

Referring to FIG. 6, in the breath analyzing apparatus 12 of the invention, the desorbing means 20, the precolumn 16 and the main column 14 are connected for analysis of the concentrated breath sample. The sample receiving tube and the sample loop 18 are connected as well to sample the breath exhaled by the subject. Further, the sample loop 18 and the main column 14 are connected to analyze the breath sample sucked into the sample loop 18. Then, the standard gas bottle 62, the sample loop 18 and the main column 14 are connected to test sensitivity of the detector 56 and calculate a resolution representing the column performance by the use of the standard gas.

Constituents of the standard gas, the breath breathed out by the subject or the breath concentrated in the absorbent sample tube are detected in the same main column 14 and detector 56, and analyzed in the data processing means 72. Adoption of the configuration shown in FIG. 6 makes it possible to analyze low-concentration and high-concentration breath constituents, and makes it easier to carry out a test by the use of the standard gas.

The precolumn 16, being provided for backflash, is not used for sampling breath from the sample receiving tube. When conducting backflash, the carrier gas should be sent to the main column while purging constituents remaining in the precolumn. When sampling breath with the sample receiving tube, the breath should be sucked into the sample loop by means of the pump at an end, and then sent to the main column by means of the carrier gas. The configuration shown in FIGS. 1 and 2 is an embodiment permitting achievement of the steps mentioned above, but any other configuration may be adopted, such as one based on opening/closing of the solenoid valve.

Figure 7:
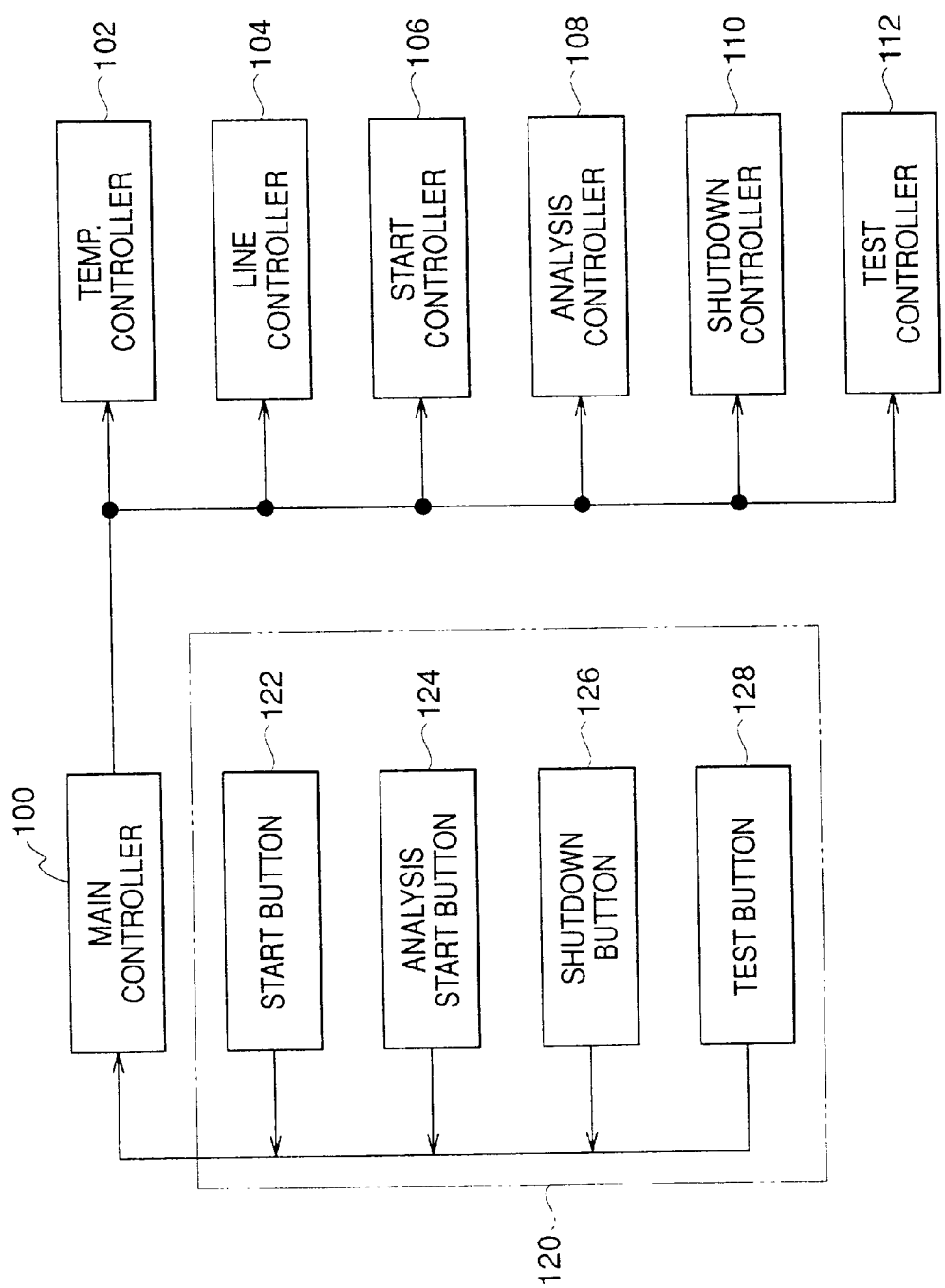
FIG. 7 is a block diagram illustrating the configuration of the controller.

Referring to FIG. 7, the controller 44 comprises a main controller 100, temperature controller 102 for controlling the individual heaters, and line controller (channel controller) 104 for controlling switching of the channels. Further, in this embodiment, the apparatus comprises start controller 106 for controlling the breath analyzing apparatus from stationary to a state capable of accomplishing analysis, analysis controller 108 for controlling analyzing operations, shutdown controller 110 for discontinuing operation of the breath analyzing apparatus upon completion of analysis, and test controller for testing performance of the breath analyzing apparatus by the use of the standard gas.

Further, an interface 120 is connected to the controller 44. The interface 120 comprises a start button 122 for user's instructing start of the breath analyzing apparatus, an analysis start button 124 for instructing start of analysis, an end button for instructing end of analysis, and a test button 128 for instructing testing. A button for switching over between concentrated and non-concentrated types, or setting an object to be analyzed may be provided.

Referring to FIG. 8, the temperature control means 102 is provided with preselected temp. recorder 130 for storing set temperature and a heater driver 132. The recorder 130 stores temperatures forming conditions for analysis such as a column temperature set in response to the material to be breath-analyzed. The heater driver 132 is connected to the column heater 14H, the detector heater 56H, the absorbent sample tube heater 22H, the secondary concentrating tube heater 26H and the thermostatic oven 42H.

Figure 9:
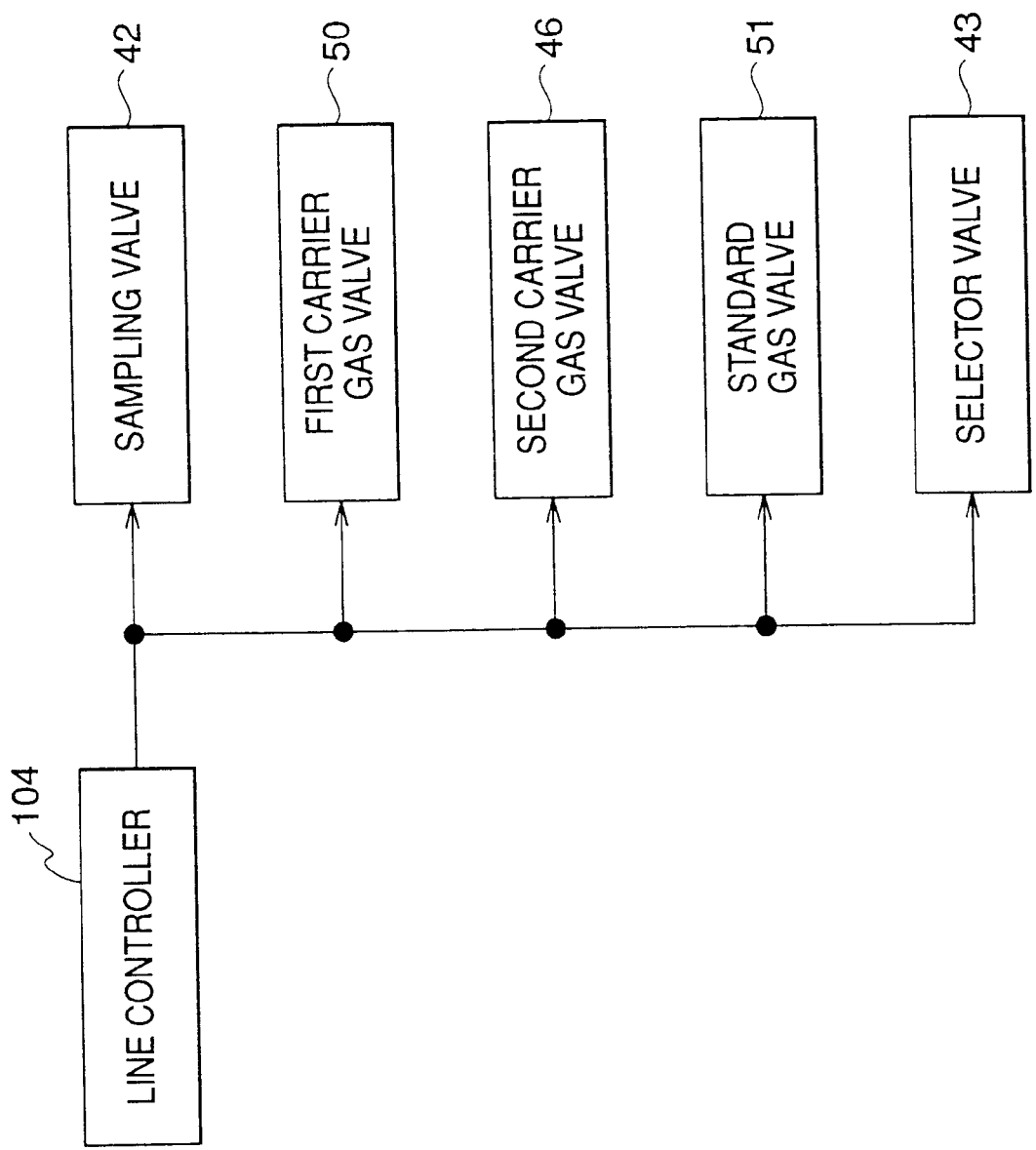
FIG. 9 is a block diagram illustrating the configuration of channel switching means.

Referring to FIG. 9, the line controller 104 is connected to the sample valve 42, the first carrier gas solenoid valve 50, the second carrier gas solenoid valve 46, the standard gas valve 51 and the standard gas switching valve (select valve) 43.

The controller 44 controls start, shutdown, testing and analysis of the breath analyzing apparatus by performing control with reference to the temperature and the switching time.

Operation

Figure 10:
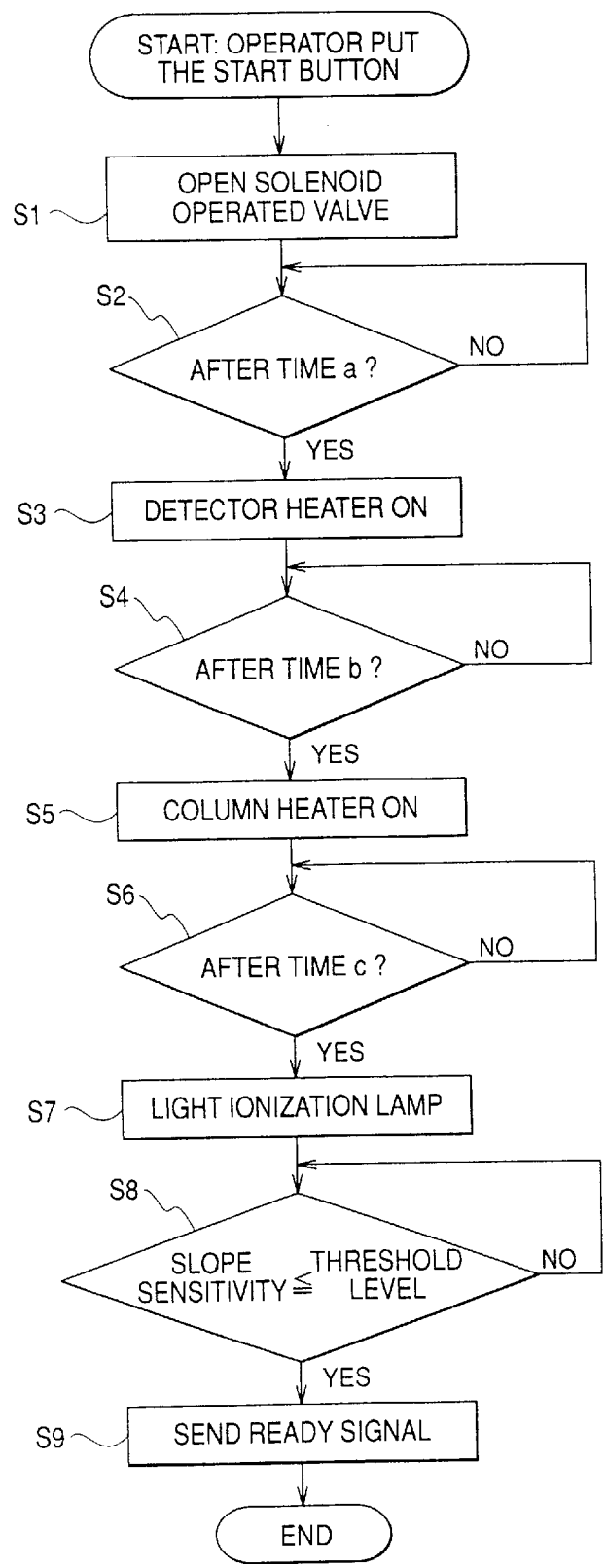
FIG. 10 is a flowchart illustrating a typical start processing using the time.

Start processing using time:

Referring to FIG. 10, when the subject presses the start button 122, start operation by the controller 44 is started. First, the controller 44 selects a channel for startup, and opens the carrier gas solenoid valves 50 and 46 (S1). The channel for starting purges the main column 14 and the detector 56, and serves also as a channel for purging the desorbing means (FIG. 2). Referring again to FIG. 2, the carrier gas, which is introduced from the desorbing means into the precolumn, may be purged in the reverse direction from the port 8, i.e., from the precolumn 16 to the desorbing means 20.

The timing when the solenoid valve 50 is opened is regarded as the starting point, i.e., 0 minute. Thereafter, it is determined whether or not a certain period of time a has elapsed (S2). As a result, the carrier gas C purges the main column 14 and the detector 56, and then, the precolumn 16 and the desorbing means 20. This certain period of time a is for example three minutes.

After the lapse of the certain period of time a, the detector heater 56H is turned on (S3; lapse of three minutes). Then, it is determined whether another certain period of time b has elapsed (S4). After the lapse of the certain period of time b, the column heater 14H is turned on (S5; lapse of ten minutes). The certain period of time b is set by comparing heating properties of the detector heater 56H and the column heater 14H so that the detector temperature is always higher than the column temperature. The certain period of time b is for example seven minutes.

Further, it is determined whether or not a certain period of time c has elapsed (S6). After the lapse of the certain period of time c, the ionization lamp 58 of the detector is turned on (S7; lapse of 13 minutes). The certain period of time c should be set at a value not reducing the period of time available for the ionization lamp 58 by stabilization of operations of the ionization lamp 58 before operations of the detector 56 are not as yet stabilized. The certain period of time c is for example three minutes.

Further, when an output signal from the detector 56 shows a value under a prescribed value (3 V for example), confirmation of slope sensitivity is started, and it is determined whether or not the slope sensitivity takes a value under a certain value (200 $\mu$V/min for example) (S8). When the slope sensitivity becomes under a certain value, a preparation completion signal is issued (S9; lapse of 43 minutes). As a result, preparation completion is displayed on the display 34. A slope sensitivity under the certain value means that residual constituents leaving the main column decrease and operation of the detector 56 has become stable.

Figure 11:
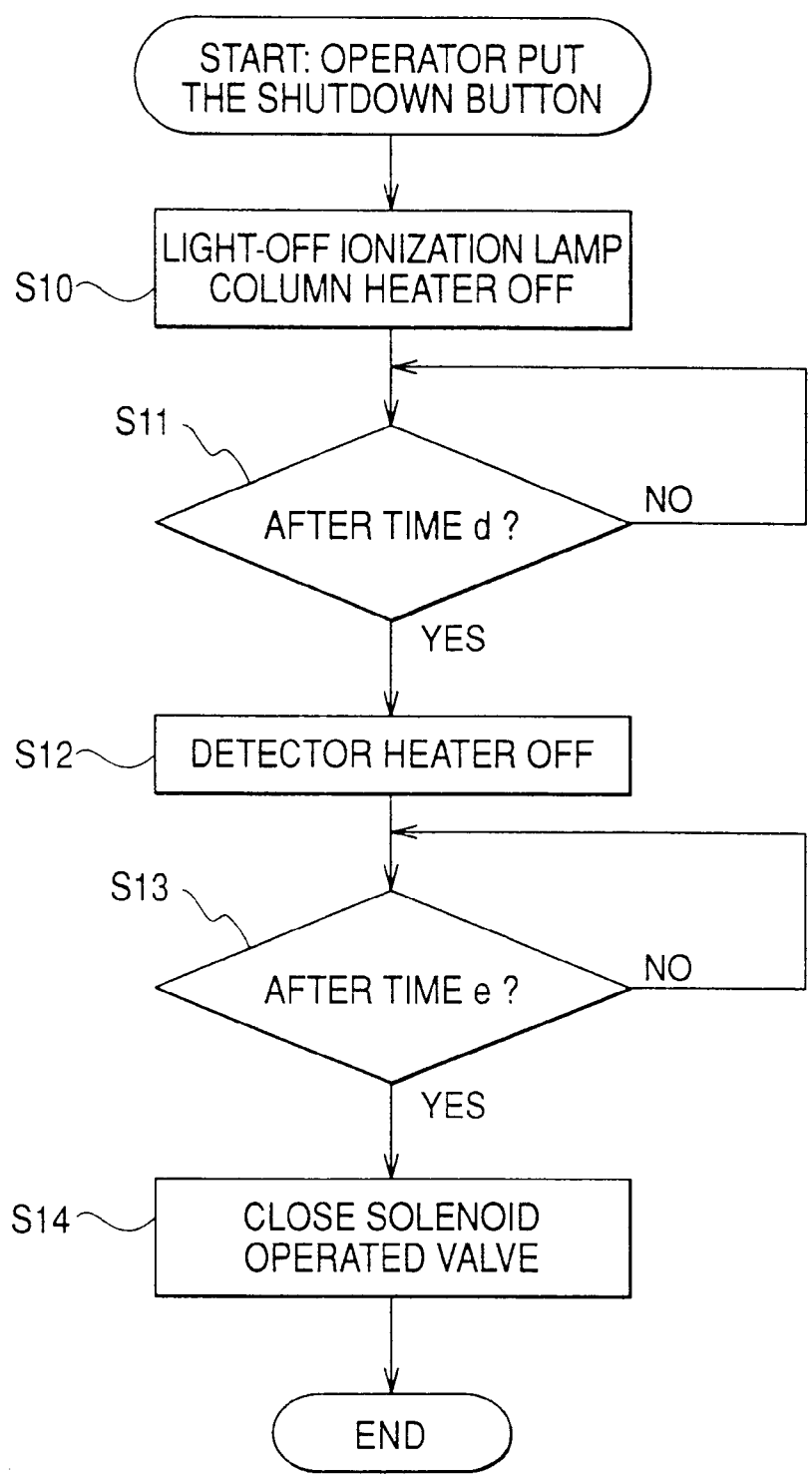
FIG. 11 is a flowchart illustrating a typical and processing using the time.

Shutdown processing using time:

Referring to FIG. 11, when the operator presses the shutdown button 126, the end operation by the controller 44 is started. The controller 44 selects a channel for starting and finishing from among the various channels for analysis. It further turns off the ionization lamp 58, and turns off the column heater 14H (S10). The moment when the column heater 14H is turned off is regarded as 0 minute. Then, it is determined whether or not a certain period of time d has elapsed (S111). Upon the lapse of the certain period of time d, the detector heater 16H is turned off (S12; lapse of one minute). The certain period of time d is set by comparing cooling properties between the detector heater 16H and the column heater 14H so that the detector temperature is always higher than the column temperature. The period of time d is for example one minute.

Then, it is determined whether or not a certain period of time e has elapsed (S13). Upon the lapse of the certain period of time e, the solenoid valve 18 is closed (S14; lapse of 36 minutes). The certain period of time e is set by taking account of the cooling property of the detector heater 16H so as to cause degradation of performance of the detector 56 as a result of the high-temperature detector 56 coming into contact with the open air. The certain period of time e is for example 35 minutes.

Figure 12:
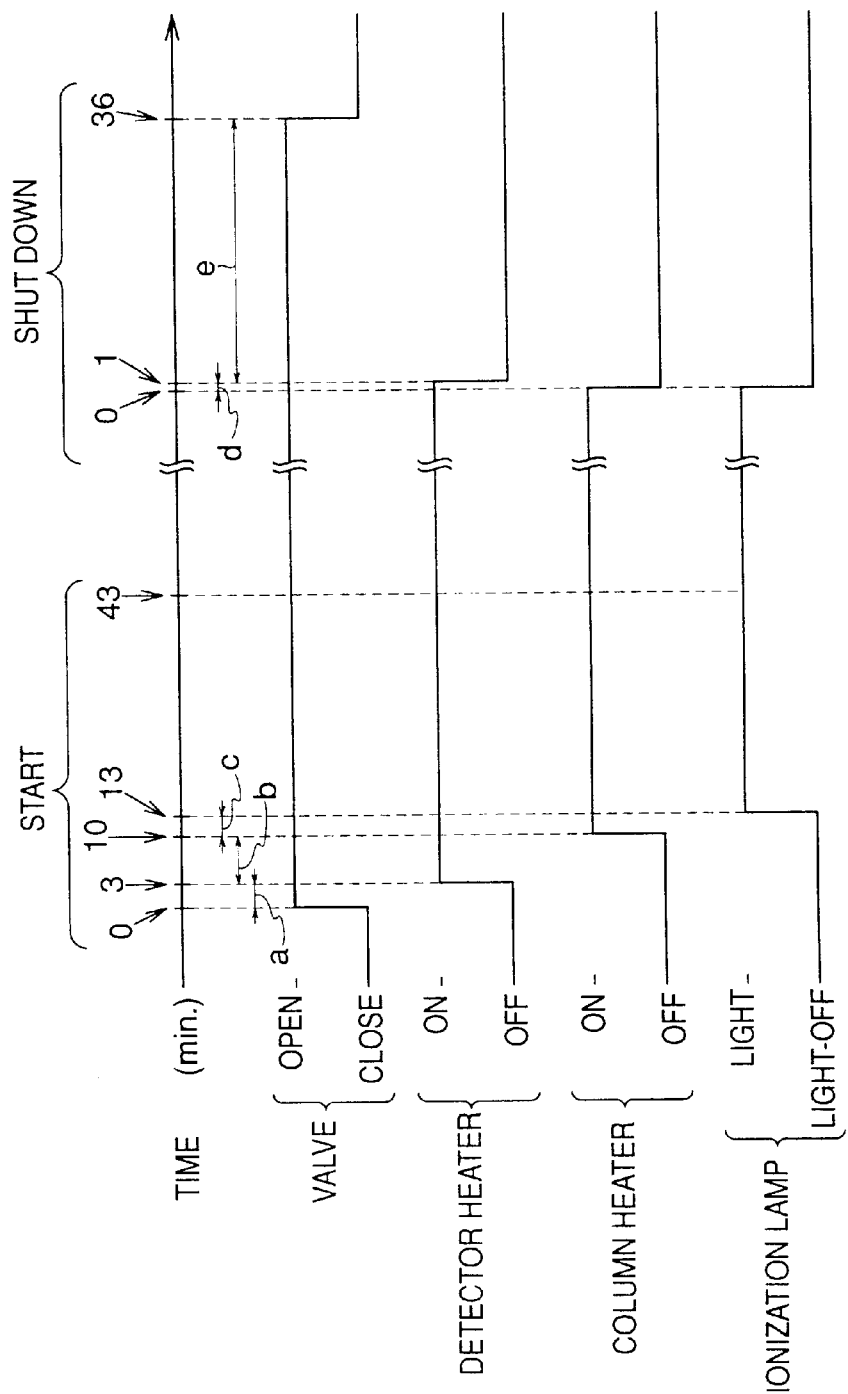
FIG. 12 is a time chart of the processing shown in FIGS. 10 and 11.

More specifically, the controller 44 controls the solenoid valve, the detector heater, the column heater and the ionization lamp in accordance with the time chart shown in FIG. 12, thereby achieving the foregoing flowchart.

Figure 13:
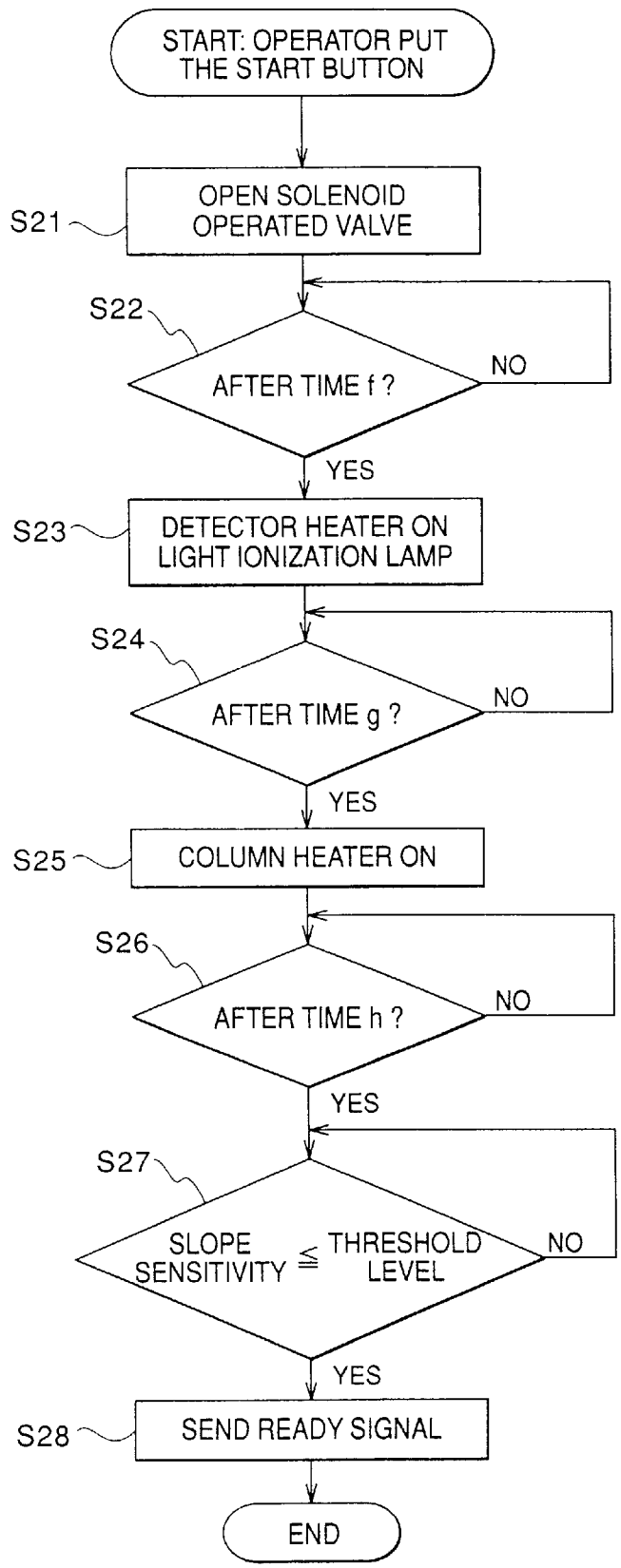
FIG. 13 is a flowchart illustrating another example of start processing using the time.
Figure 14:
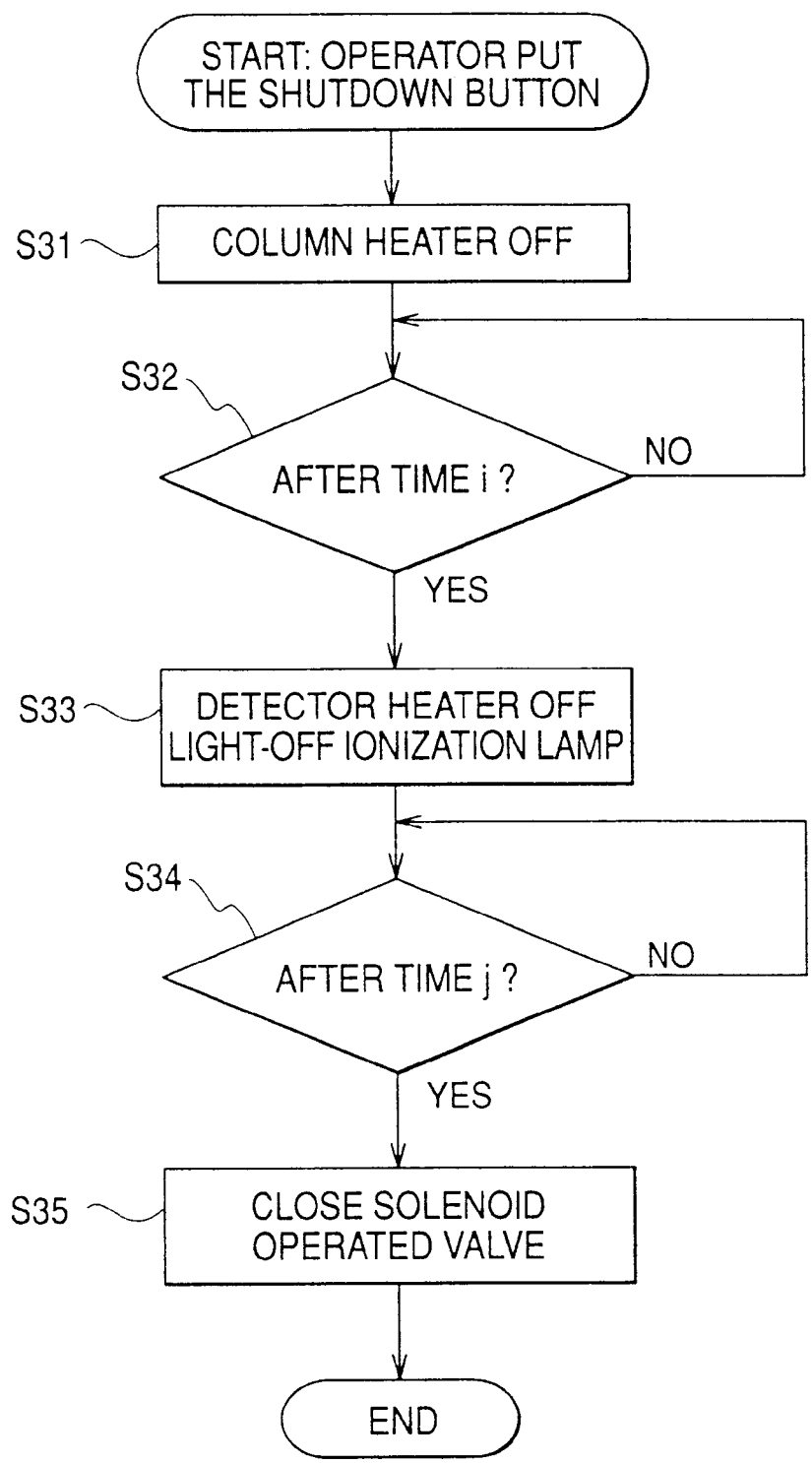
FIG. 14 is a flowchart illustrating another example of end processing using the time.
Figure 15:
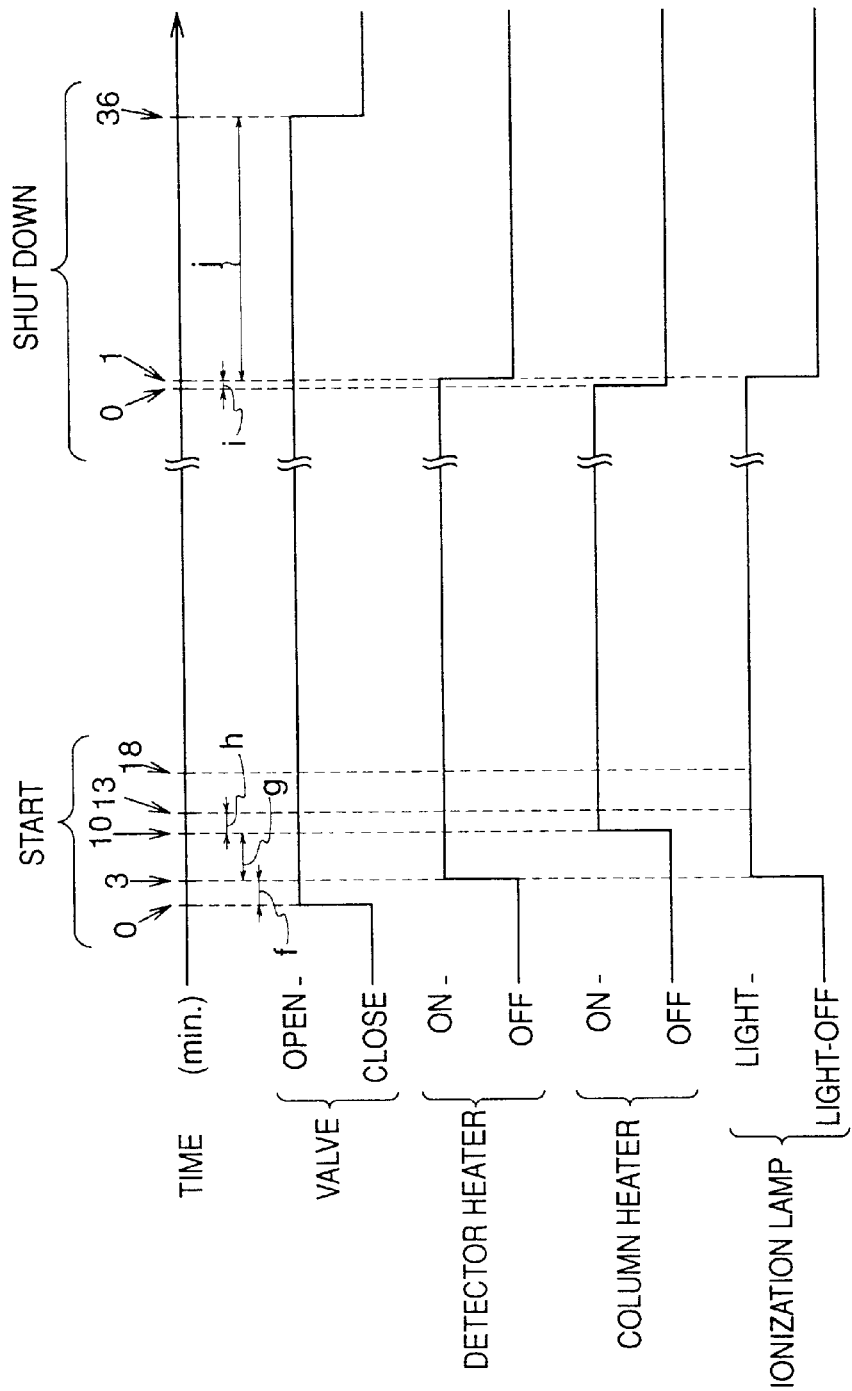
FIG. 15 is a time chart of the processing shown in FIGS. 13 and 14.

Another example of start or end control using time:

Referring to FIG. 13, upon starting, the controller 44 turns on the ionization lamp simultaneously with turn-on of the detector heater (S23). In the example shown in FIG. 13, the startup time can be reduced. Referring to FIG. 14, the controller 44 turns off the ionization lamp simultaneously with turn-off of the detector heater (S33). This flowchart is achieved by the controller 44 operating in accordance with the time chart shown in FIG. 15.

Figure 16:
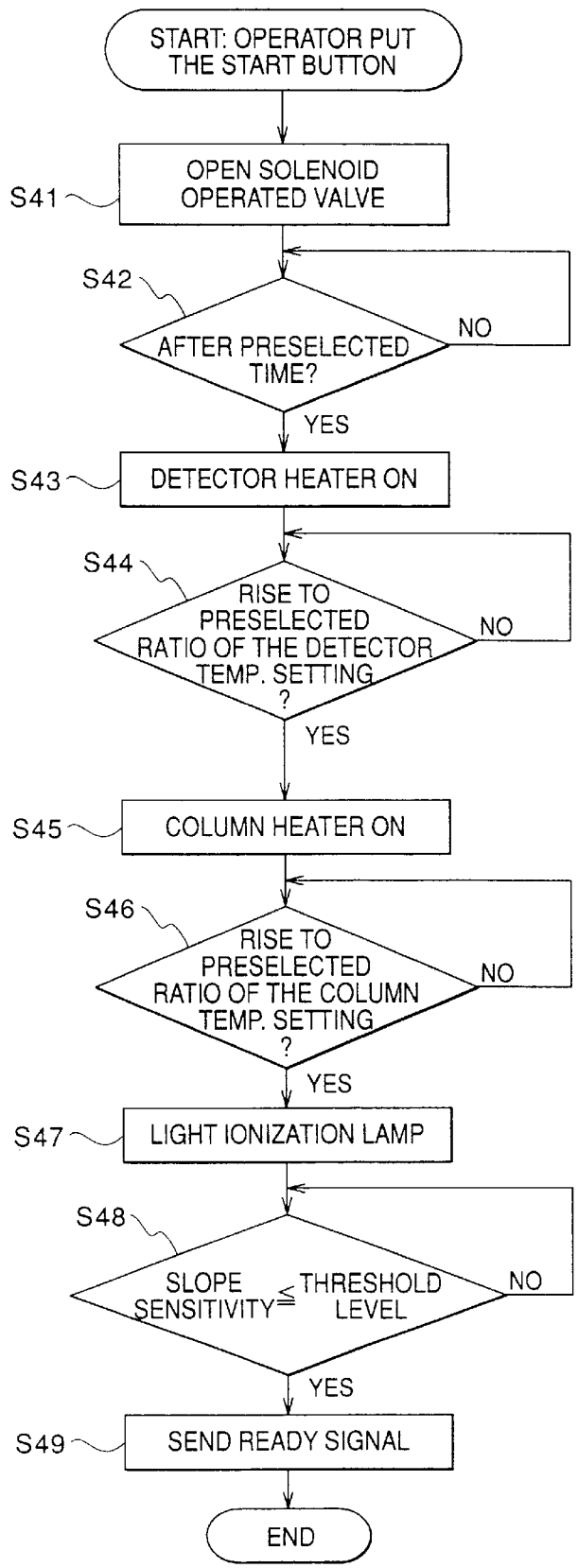
FIG. 16 is a flowchart illustrating an example of start processing using the time.

Start processing using temperature:

Referring to FIG. 16, when the operator presses the start button 122, the start operation by the controller 44 is started. First, the controller 44 selects the channel for starting and opens the solenoid valve (S41). The moment when the solenoid valve opens is regarded as 0 minute. Then, it is determined whether or not a certain period of time has elapsed (S42). The certain period of time is for example three minutes. Upon the lapse of the certain period of time, the detector heater 16H is turned on (S43; lapse of three minutes), and it is determined whether or not the detector 56 temperature has reached a certain percentage of the set detector temperature (S44). The set detector temperature is stored in the set temperature storing means 130. When the temperature has reached a certain percentage, the column heater 14H is turned on (S45; lapse of eight minutes). The set detector temperature is 120° C., and the certain percentage is 60% corresponding to about 70° C. This certain percentage is set at a value such that the temperature of the column 14 becoming higher than that of the detector 56 does not impair accuracy of the detector 56.

Then, it is determined whether or not temperature of the column 14 has reached the certain percentage of the set temperature (S46), and upon reaching the certain percentage, the ionization lamp 58 is turned on (S47; lapse of ten minutes). The set column temperature is 100° C., and the certain percentage is 80% corresponding to 80° C. This certain percentage is set at such a value that the available period of time for the ionization lamp 58 is never reduced by the stabilization of operation of the ionization lamp 58 before stabilization of operation of the detector 56.

Then, when the output signal of the detector 56 shows a value under a certain value (3 V for example), confirmation of slope sensitivity is started, and it is determined whether or not the slope sensitivity has become under a certain value (S48). When the slope sensitivity becomes under the certain value, a preparation completion signal is generated for output (S49; lapse of 37 minutes). As a result, preparation completion is displayed on the display.

Figure 17:
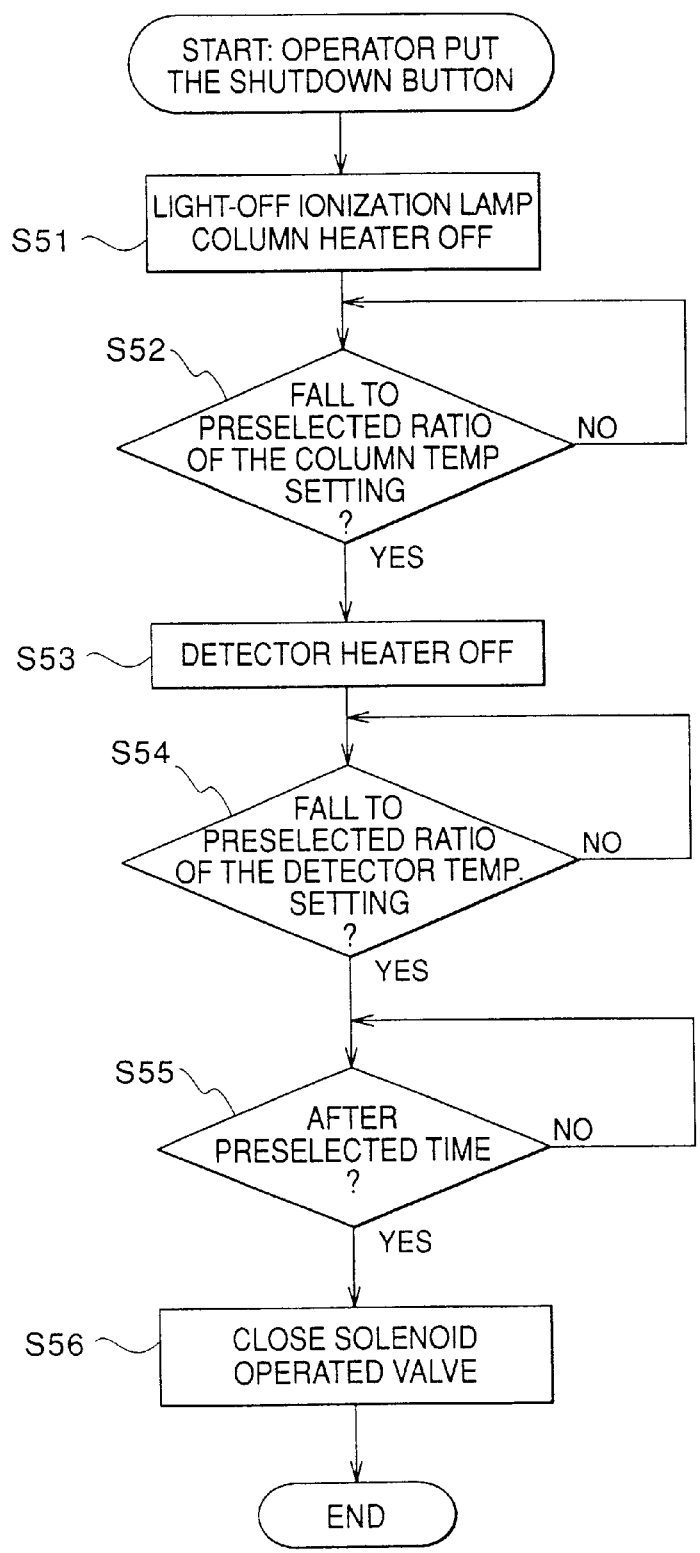
FIG. 17 is a flowchart illustrating an example of end processing using the time.

Shutdown processing using temperature:

Referring to FIG. 17, when the operator presses the shutdown button 126, end operation by the controller 44 is started. First, the controller 44 selects a channel for start and end, turns off the ionization lamp 58, and turns off the column heater 14H (S51). This is regarded as the starting point, i.e., 0 minute. Then, it is determined whether or not temperature of the column 12 has reached a certain percentage of the set column temperature (S52), and when it decreases to the certain percentage, the detector heater 56H is turned off (S53; lapse of one minute). The set column temperature is 100° C., and the certain percentage is 70% corresponding to 70° C. This certain percentage is set at such a value that accuracy of the detector 56 is never degraded by the temperature of the detector 56 becoming lower than that of the column 12.

Figure 18:
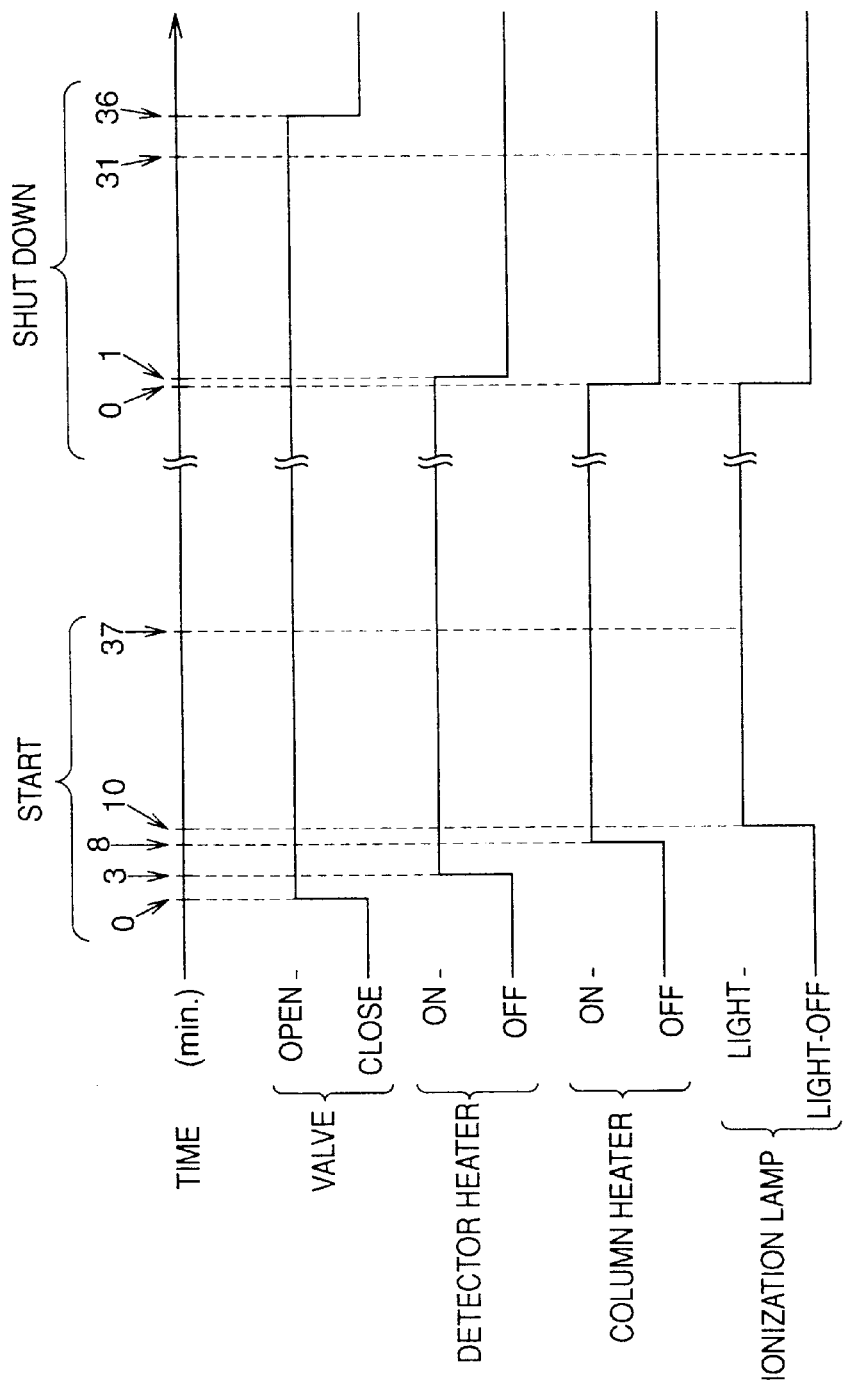
FIG. 18 is a time chart of the processing shown in FIGS. 16 and 17.

Then, it is determined whether or not temperature of the detector 56 has decreased to the certain percentage of the set detector temperature (S54). When it decreases to the certain percentage, it is determined whether or not a certain period of time has elapsed (step S55; lapse of 31 minutes). Upon the lapse of the certain period of time, the solenoid valve is closed (S56; lapse of 36 minutes). The set detector temperature is 120° C., and the certain percentage is about 17% corresponding to 20° C. The certain period of time is five minutes. The certain percentage and the certain period of time are set at such values that performance of the detector 56 is never degraded by the high-temperature detector 56 exposed to the open air. Start and end control using temperature results in a time chart for example as shown in FIG. 18.

Concentrated type test processing:

Referring to FIG. 19, when the test button 128 is pressed, the controller 44 tests the column 14 and the detector 56. First, the valve 42 is driven to the second operating position as shown in FIG. 2, and the solenoid valve is opened. Then, the carrier gas C is sent through the sample loop 18 to the main column 14 and the detector 56. Then, slope sensitivity of the detector 56 is measured (S61). Typical test conditions include a column 12 temperature of 80° C., a detector 56 temperature of 120° C. and a carrier gas C comprising helium at 6 ml/min.

Then, the sample valve 42 is switched over to the first operating position as shown in FIG. 1. The standard gas valve 43 is switched over and the solenoid valve 48 is opened to standard gas in a certain quantity is introduced into the sample loop 18. Further, the sample valve 42 is switched over to the second operating position as shown in FIG. 2. Then, the solenoid valve 46 is opened to send the standard gas S introduced into the sample loop to the main column 14 and the detector 56.

Since the standard gas contains pentane and isoprene in concentrations contained in the breath sample desorbed in the desorbing means 22, the main column 14 separates these constituents in response to the respective retention times. The detector 56 generates electric signals dependent on the content of each constituent by ionizing the breath constituents by irradiating, for example, the ionization lamp 58. Further, the data processor 72 calculates resolutions from chromatographs of pentane and isoprene (S62).

Figure 20:
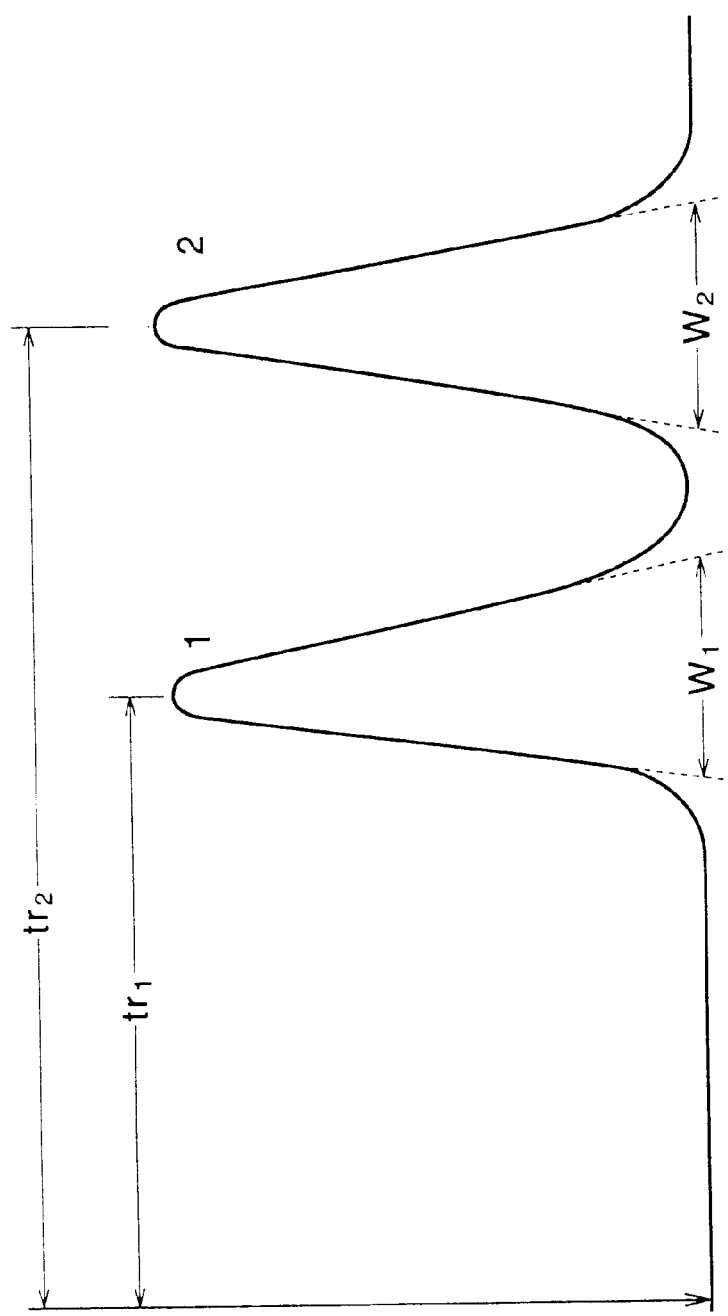
FIG. 20 is a graph illustrating typical conditions for conditioning.

Referring to FIG. 20, the extent of separation of the two constituents cannot be known from the separation coefficient k (the keeping ratio of the latter constituent relative to the former constituent, k>1) and the steepness of peaks of both constituents (theoretical number of steps, N) alone. An extent of separation can be expressed by a resolution R. In FIG. 20, R is given by:

$$R=2(tr2-tr1)/(w1-w2)$$

The following formula can be derived as a formula correlating R with N, k and k' on the assumption of w1=w2:

$$R=(N1/2/4)[k-1]/\alpha[k'/(k'+1)]$$

When R<0.5, two peaks almost overlap each other, R=1 leads to partial overlap of 2%, and R=1.25, to overlap of 0.5%. With R=1.5, separation is substantially complete.

Then, it is determined whether or not sensitivity of the detector 56 and resolution of the column 12 are normal (S63). A sensitivity of the detector 56 as represented by a slope sensitivity under a certain value (200 $\mu$V for example) is normal, and one over the certain value is abnormal. A column 12 resolution of over a certain value is normal, and one under the certain value is abnormal. The certain value for resolution is equal to a threshold value of 1.5 when the standard gas comprises a combination of helium with isoprene and pentane.

Figure 21:
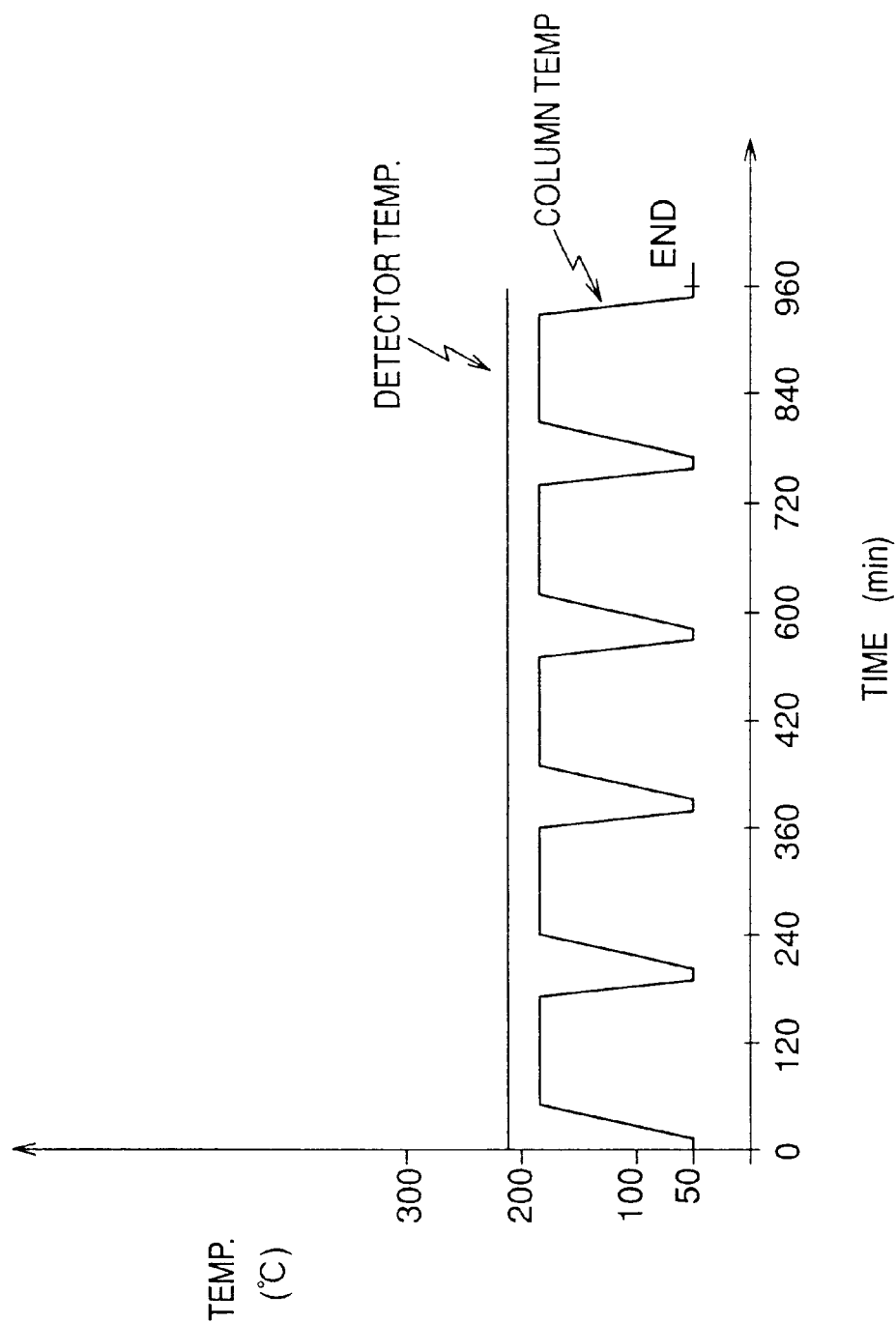
FIG. 21 is a time chart.

If sensitivity of the detector 56 or resolution of the column 14 is abnormal, the column 14 and the detector 56 are conditioned (S64). Conditioning is carried out by supplying the carrier gas for a certain period of time while heating the main column 14 and the detector 56. Referring to FIG. 21, the carrier gas is supplied for 960 minutes. In this supply, temperature of the column 14 is varied within a range of from 50° C. to near the maximum temperature. Temperature of the detector 56 is kept constant. Of the carrier gas C, helium is supplied at 6 ml/min.

Upon completion of this conditioning, sensitivity of the detector 56 is tested again (S65), and resolution of the column 12 is tested (S66), to determine whether or not sensitivity of the detector 56 and resolution of the column 12 are normal (S67). When sensitivity of the detector 56 or resolution of the column 12 is abnormal, this is displayed on the display 34 (S68). The display tells, when sensitivity of the detector 56 is abnormal, that "The detector may deteriorate. Check or replace the detector." and when resolution of the column 12 is abnormal, that "The column may deteriorate. Check or replace the column." As required, execution of automatic end causes end of all the operations (S69).

When no abnormality is found in steps S64 and S67, execution of automatic end (S69) causes end of all the operations.

In an embodiment, timing of starting test is not only pressing the test button 128, but the column 14 and the detector 56 are tested at every lapse of a prescribed period of time or every end of a prescribed number of analyzing runs. The prescribed period of time in this case is for example one day, and the prescribed number runs of analysis is for example one span. One span means a number of runs of analysis when continuously analyzing the same constituent, or when continuously analyzing under the same conditions. A test may be carried out upon every end processing.

Figure 22:
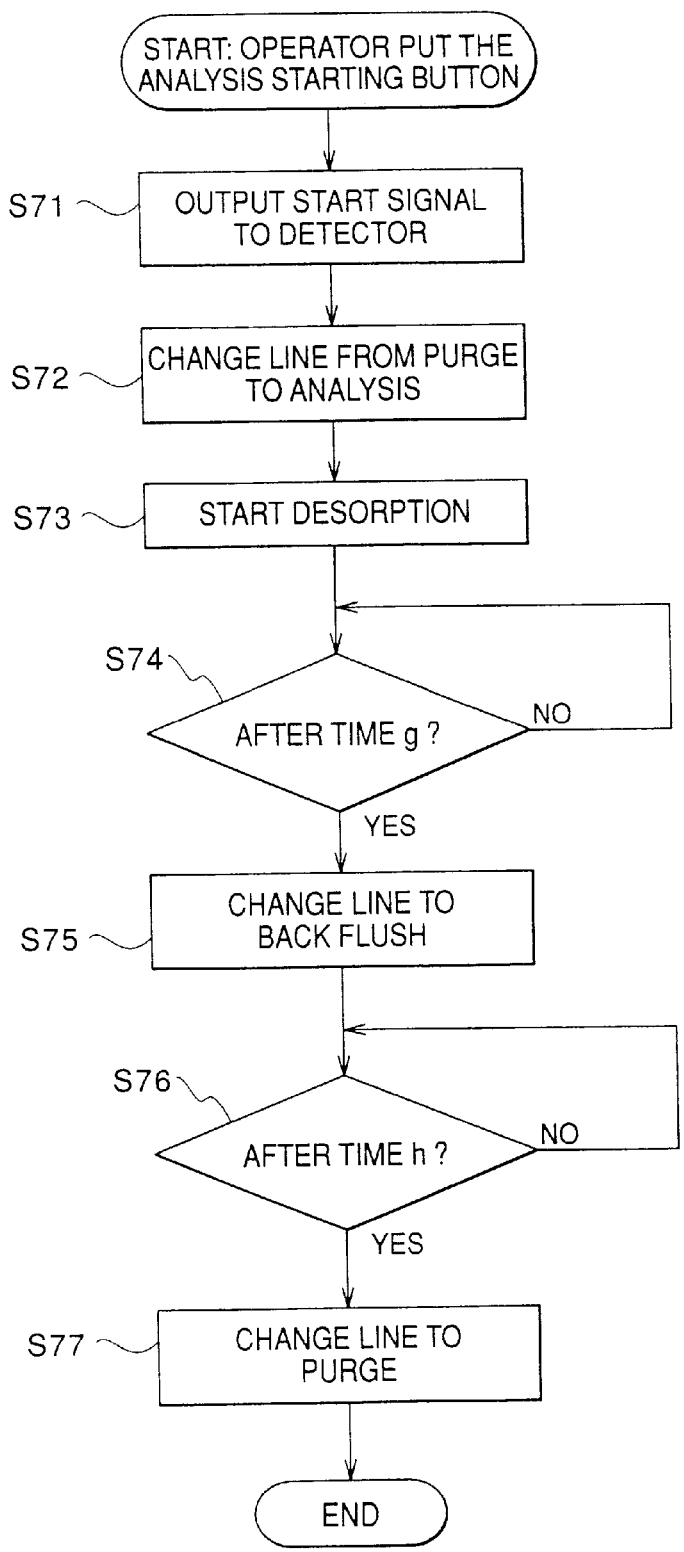
FIG. 22 is a flowchart illustrating a typical analysis processing.

Concentrated type analyzing processing:

Prior to starting analysis, the operator should previously cause the absorbent sample tube 22 to absorb the breath sample A by means of the breath concentrating/absorbing apparatus 80 shown in FIG. 5. Then, the absorbent sample tube 22 is attached to the desorbing means 20. When the operator presses the analysis start button, the controller 44 starts breath analysis. When startup has not as yet been conducted, the start processing is performed first. Upon completion of startup, the carrier gas flows constantly to purge the column 14 and the detector 56. The detector 56 always provides an output of detection signal of constituents to the data processor 72. Referring to FIG. 22, upon starting analysis, a start signal is sent to the data processor 72 (S71). Then, the data processor 72 stores the output signal from the detector 56.

Then, the controller switches over the channel from the purging channel to that shown in FIG. 1 (S72). Then, the breath sample absorbed in the absorbent sample tube is desorbed. Appearance of a peak in the chromatograph varies with the manner of desorbing. That is, a gradual desorbing result in an excessively wide band, preventing satisfactory quantitative determination. In this embodiment, therefore, a secondary concentration is performed.

Figure 23:
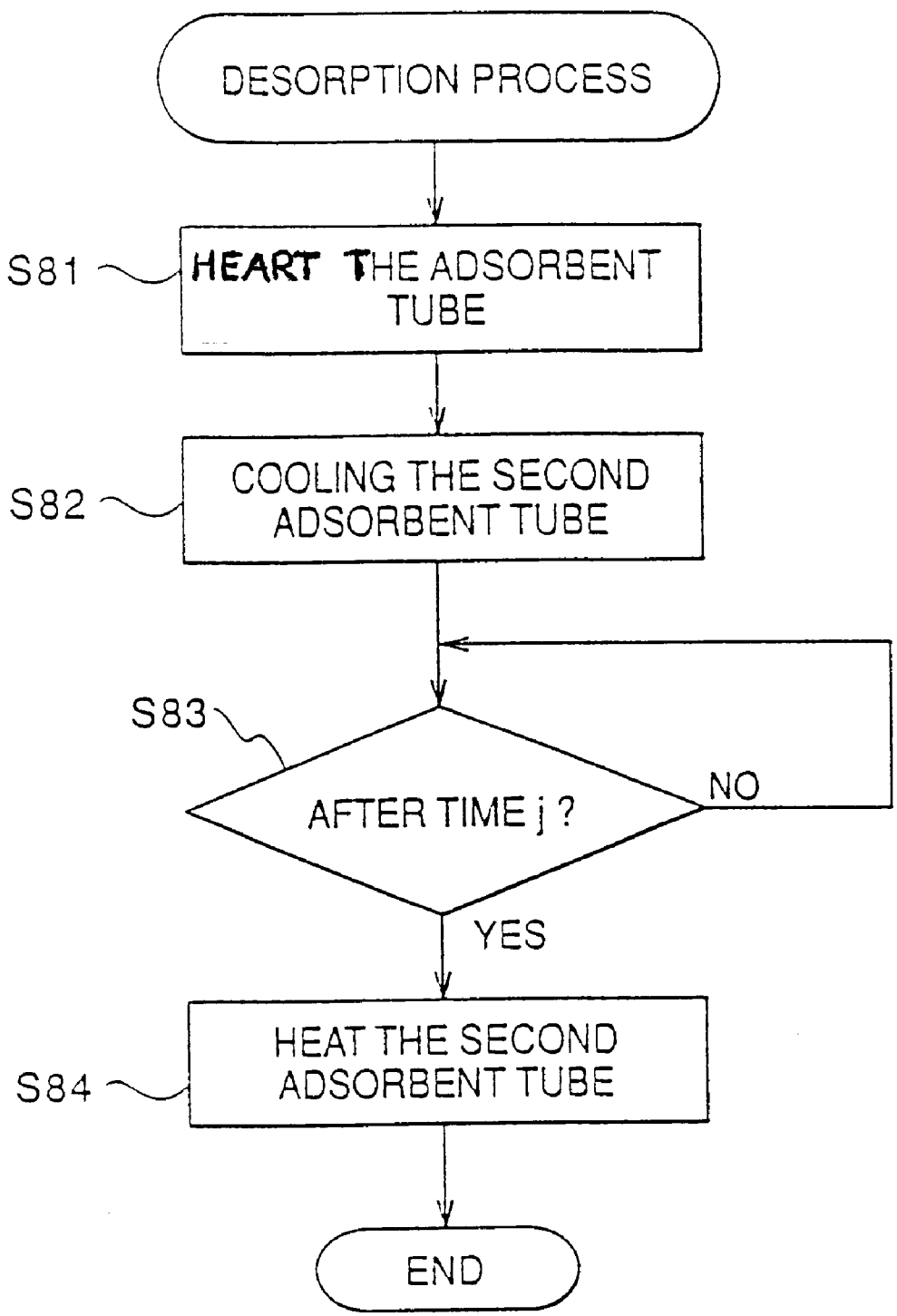
FIG. 23 is a flowchart illustrating an example of desorbing processing.

Referring to FIG. 23, the desorbing processing S73 comprises heating the absorbent sample tube 22 for example to 250° C. (S81), and at the same time, cooling the secondary concentrating tube 26 for example to a temperature within a range of from −130 to −180° C. (S82). When the carrier gas C is passed from the absorbent sample tube 22 to the secondary concentrating tube 26, the breath sample A leaves the absorbent sample tube 22, is further concentrated, and absorbed by the secondary concentrating tube 26. Upon completion of absorption of the breath sample A into the secondary concentrating tube 26, i.e., upon the lapse of a certain period of time j (S83), the secondary concentrating tube 26 is heated for example to 190° C. (S84).

Referring again to FIG. 1, at this point, the solenoid valve 46 is closed to saving the carrier gas C. The carrier gas C1 therefore flows through the solenoid valve 50, the desorbing means 20, the filter 30, the ports 10 and 9, the precolumn 16, the parts 1 and 2, the main column 14, and the detector 56, and then discharged. The breath sample A flow as well with the carrier gas C, and passes through the precolumn 16, the main column 14 and the detector 56. Constituents contained in the breath sample A are separated in the precolumn 16 and the main column 14, and are thus detected by the detector 56 with time changes.

In the concentrated type, it is possible to detect low-concentration high-boiling-point constituents (such as hexane) which cannot be detected in the non-concentrated type. However, ordinary high-boiling-point constituents have a long retention time in the precolumn 16 and the main column 14 (delay in retention). As a result, the time required for analysis, which is for example 15 minutes in the non-concentrated type, is more than an hour in the concentrated type.

Referring to FIG. 24, pentane P is detected in about six minutes from the start of analysis, and hexane H is detected in about 30 minutes. Even when only pentane P must be detected, therefore, it is necessary to continue analysis for a long period of time for discharging hexane. To pass a high-boiling-point constituent such as hexane through the main column 14 and the detector 56 may lead to contamination or deterioration of these components.

For the purpose of reducing the analyzing time and preventing contamination and deterioration, therefore, backflash is conducted. As shown in FIG. 25(A), when the carrier gas C1 begins flowing through the precolumn 16 and the main column 14, pentane P and hexane H, which are constituents of the breath sample A, enters the precolumn 16. Pentane P which is harder to be held in the precolumn 16 than hexane H passes through the precolumn 16 before hexane as shown in FIG. 25(B). As time passes and even when pentane P has advanced considerably into the main column 14, hexane still remains in the precolumn 16, as shown in FIG. 25(C). If the carrier gas C1 continues to flow in this state, it takes a long time for hexane H to leave the main column 14. Therefore, the precolumn 16 and the main column 14 are separated, and a carrier gas C3 in the reverse direction to the carrier gas C1 is caused to flow in the precolumn 16. The carrier gas C2 is caused to flow in the same direction as that of the carrier gas C1 in the main column 14. As a result, pentane P is detected upon leaving the main column 14, and hexane H is purged from the precolumn 16, as shown in FIG. 25(D).

When the column length, temperature thereof and the carrier gas flow rate are constant, the retention time of the breath constituents in the column is also constant. Purging of the precolumn shown in FIG. 25(D) is accomplished upon the lapse of a certain period of time g from the start of desorption.

Referring again to FIG. 22, upon the lapse of this certain period of time g (S74), pentane P stays in the main column 14, and hexane H, in the precolumn 16. The valve 42 is changed from FIG. 1 to FIG. 2 (S75). Upon further lapse of a certain period of time h, for example in the case shown in FIG. 24, the channel is switched over to that for purging the main column 14 and the detector 56 when three minutes have elapsed from the change into the backflush channel and eight minutes from the start of analysis (S77). In the example shown in FIG. 2, purging is accomplished by causing the carrier gas to flow without changing the channel.

In the detector 56, a qualitative analysis is carried out on the basis of the capacity (holding capacity) of carrier gas or the time (retention time) thereof before formation of discriminating bands of the individual constituents after pouring of the breath sample A, and a quantitative analysis, on the basis of the peak area or the peak height.

Non-concentrated type test processing:

First, the sample receiving tube 32 is heated for example to 40° C., and the channel shown in FIG. 1 is selected. When the subject presses the analysis start button and blows breath B into the sample receiving tube 32, the pump 66 operates only for a prescribed period of time in response thereto. In this case, the breath B flows through the sample receiving tube 32, the ports 5 and 6, the sample loop 18, the ports 3 and 4, and the pump 66, and is then discharged. As a result, the sample loop 18 is filled with the breath B as the breath sample A.

When the breath is sucked into the sample loop 18, the channel shown in FIG. 2 is selected to cause the carrier gas to flow therethrough. As the solenoid valve 46 is open at this point, the carrier gas C2 flows through the solenoid valve 46, the ports 7 and 6, the sample loop 18, the ports 3 and 2, and the main column 14 and the detector 56, and is then discharged. The breath sample A filling the sample loop 18 flows together with the carrier gas C2, and passes through the main column 14 and the detector 56. The constituents contained in the breath sample A are detected by the detector 56 with time changes as a result of separation in the main column 14.

Analytical conditions:

Concentration of dimethyl sulfide in the breath is believed to increase as a result of hepatocirrhosis or the like. Isoprene is a precursor of cholesterol, and the concentration thereof in breath is said to increase as a result of diabetes mellitus, hypertension diseases, cholelithiasis or arteriosclerosis. In pregnant intoxication, diabetes mellitus and arteriosclerosis, lipid peroxidation causes an increase in the pentane concentration in breath. By conducting concentration, using a PLOT (porous layer open tubular) column having a high liquidus polarity (for example, poraplot U), and setting the following conditions including a column temperature, a column length and a carrier gas flow rate, it is possible to satisfactorily separate pentane, isoprene and dimethyl sulfide in the foregoing breath analyzing apparatus.

The conditions for the main column 14 include, for example, a material comprising molten silica, an inside diameter within a range of from 0.3 to 1.0 [mm], a length of from about 10 to 25 [m], a coating layer thickness of from 10 to 20 [$\mu$m], a coating layer material comprising divinylbenzene ethylene glycol dimethacrylate. A layer length of the main column generally leads to a better resolution, but on the contrary, to a longer period of time required for analysis. A length within a range of from 10 to 25 [m] is therefore appropriate. As the detector 56, a flame ionization detector (FID) or a thermal conductivity detector (TCD) may be used.

Figure 26:
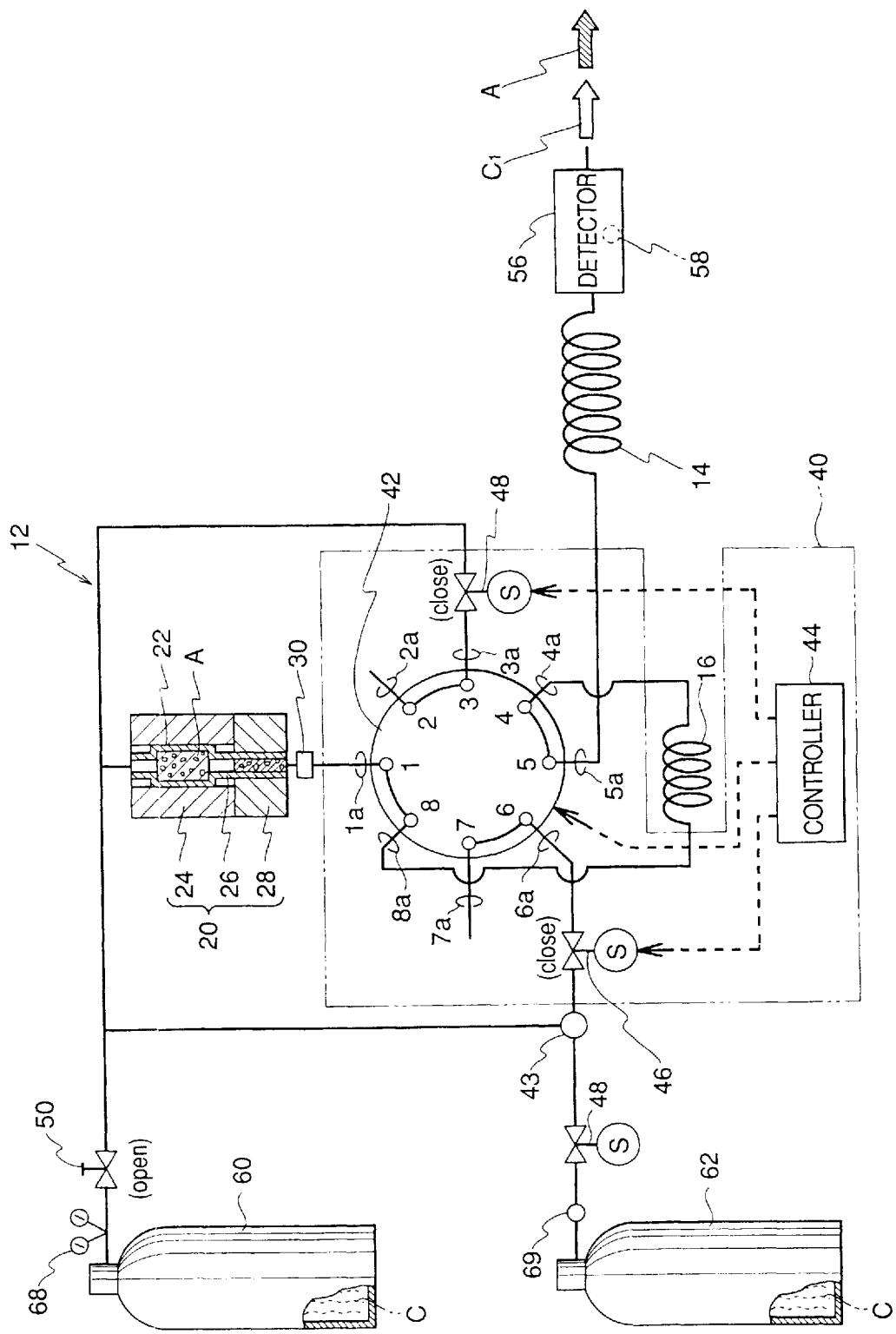
FIG. 26 is a configurational view of other embodiment of an apparatus not having a sample receiving tube.
Figure 27:
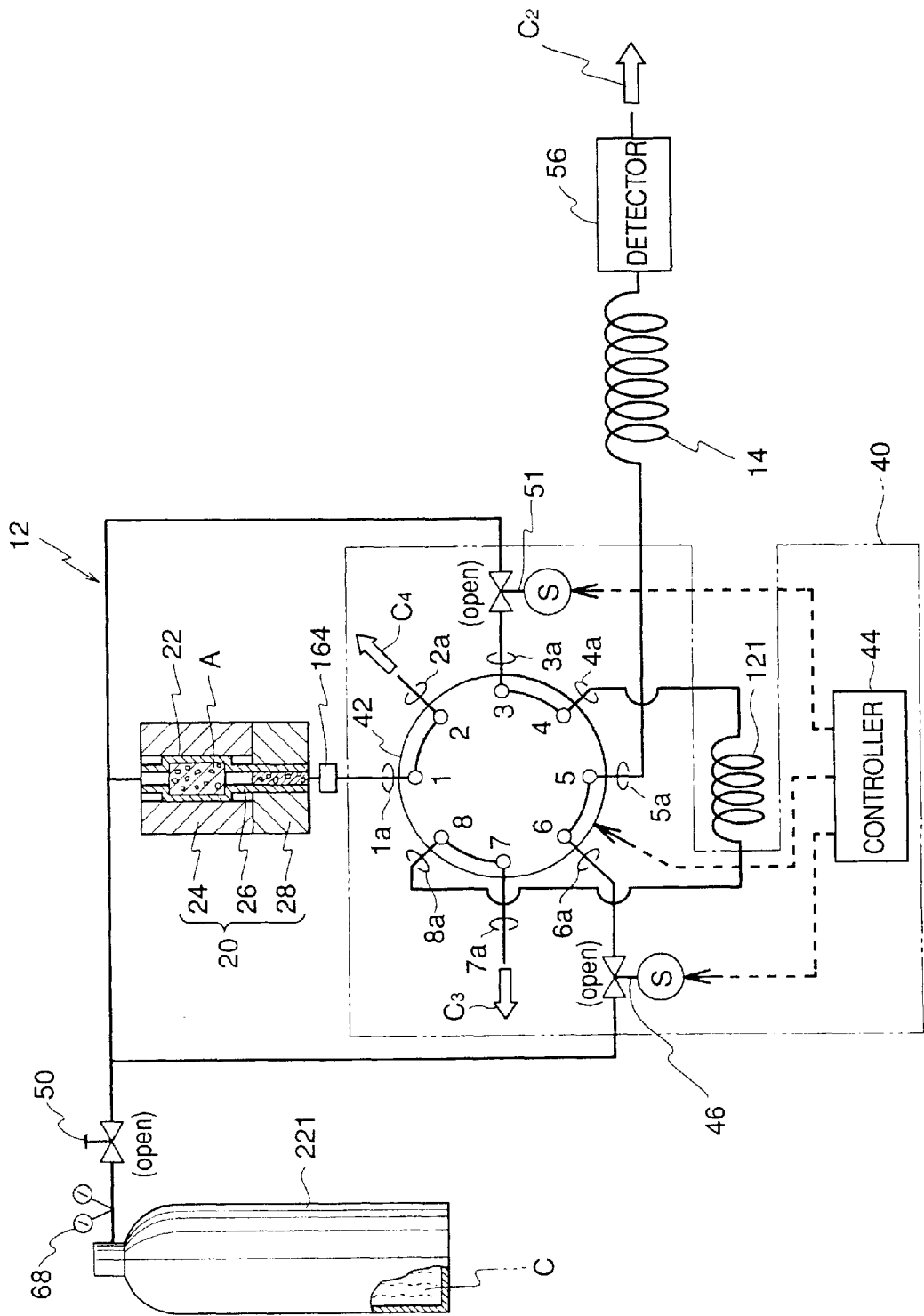
FIG. 27 is a view similar to FIG. 26, in which the sample valve is changed.

The breath analyzing apparatus shown in FIGS. 1 and 2 is employed. Since detection of pentane, dimethyl sulfide and isoprene should preferably be conducted after concentration, the sample receiving tube 32 or the sample loop 18 is not necessary for analyzing these three substances alone. A breath analyzing apparatus not having a sample receiving tube 32 is illustrated in FIGS. 26 and 27. In this example, a sampling valve 42 having eight ports is used. The carrier gases C1 to C3 upon backflash are shown in FIGS. 26 and 27. Referring to FIG. 28, the sectional view of the sampling valve 42 is substantially the same as that shown in FIG. 4.

Referring to FIG. 29, E represents a peak of ethanol, D, dimethyl sulfide, P, pentane, and I, isoprene (the same applies hereafter also in the following chromatograms). In FIG. 29, for pentane and dimethyl sulfide, the retention times become reverse under some conditions. FIG. 29[a] illustrates a case where the retention time for pentane is longer than that for dimethyl sulfide, and FIG. 29[b] covers a case where the retention time for pentane is shorter than that for dimethyl sulfide.

As is clear from FIG. 29, R12 indicates resolution for ethanol and dimethyl sulfide or pentane, R23, resolution for dimethyl sulfide and pentane, and R34, resolution for dimethyl sulfide or pentane and isoprene. As described above, reversal of the retention time between dimethyl sulfide and pentane does not affect calculation of resolution R23.

Figure 30:
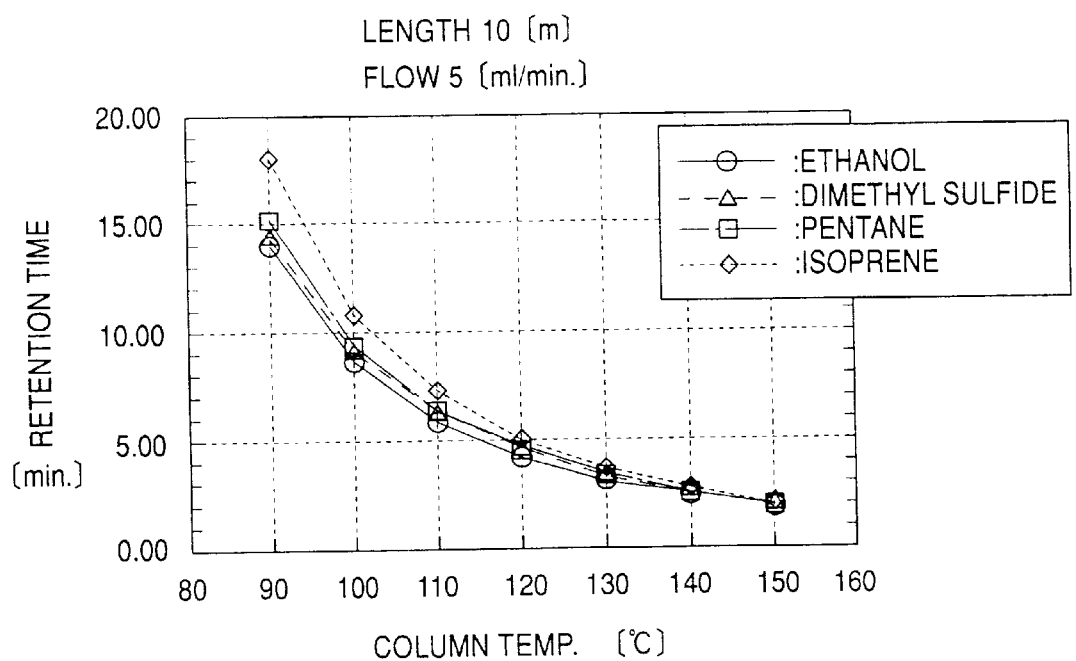
FIG. 30 is a graph illustrating retention times for the individual constituents relative to temperature of the capillary column in a capillary column having a length of 10 [m] with a carrier gas flow rate kept constant at 5 [ml/min.]
Figure 31:
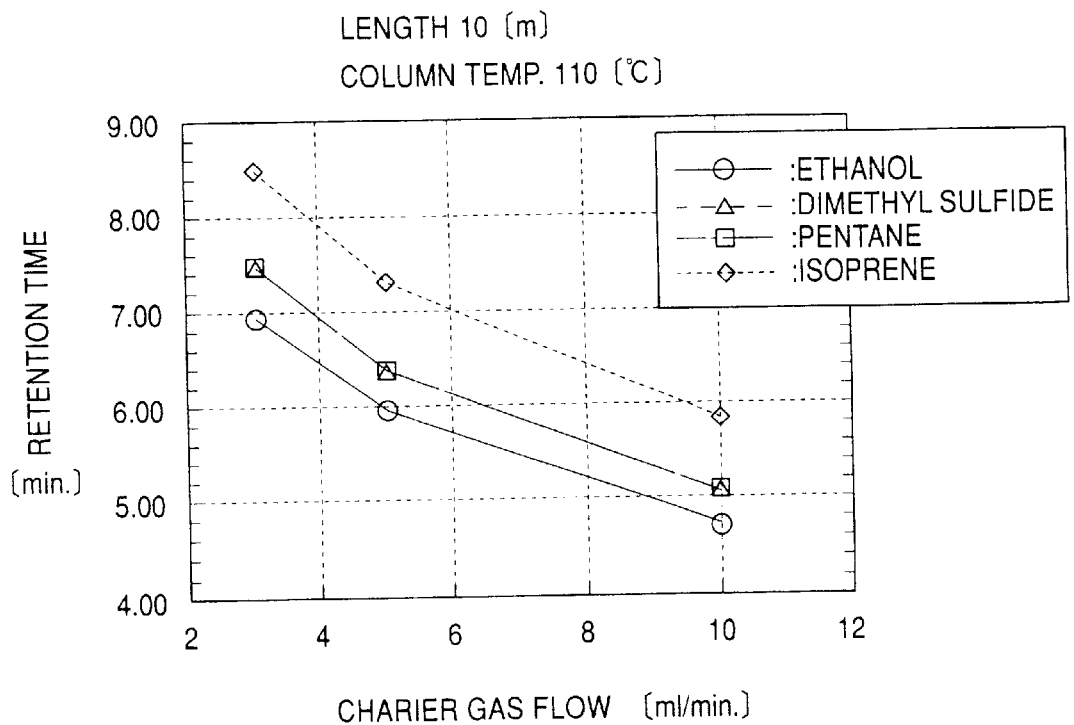
FIG. 31 is a graph illustrating retention times for the individual constituents relative to carrier gas flow rate in a capillary column having a length of 10 [m] with a capillary column temperature kept constant at 110° C.
Figure 32:
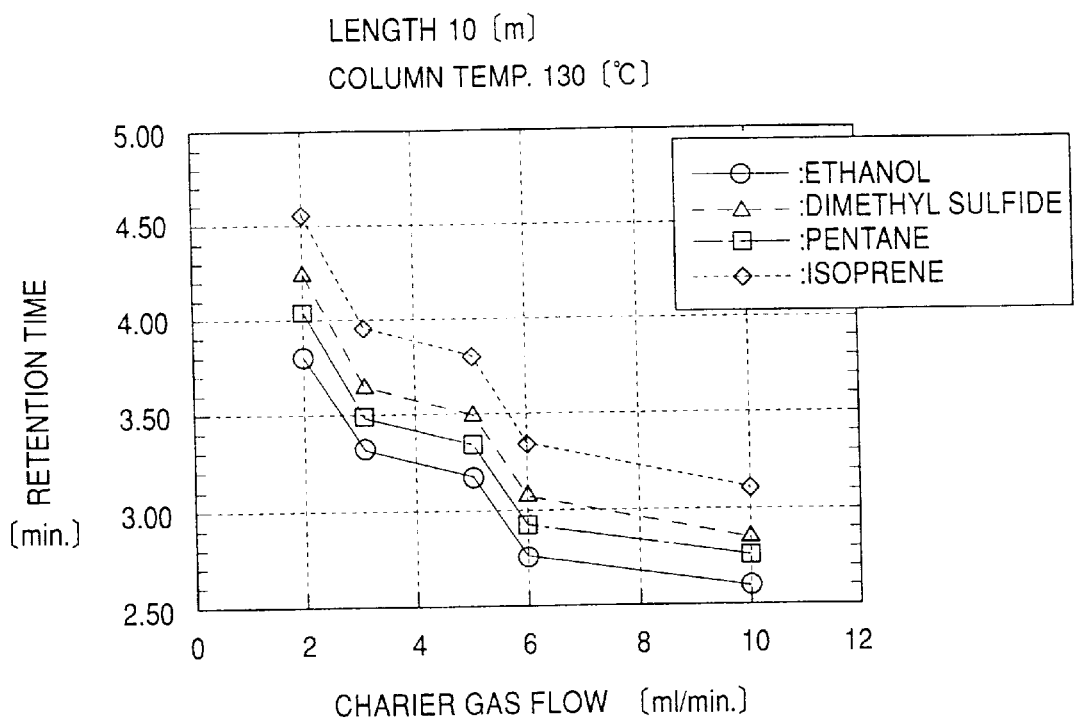
FIG. 32 is a graph illustrating retention times for the individual constituents relative to carrier gas flow rate in a capillary column having a length of 10 [m] with a capillary column temperature kept constant at 130° C.
Figure 33:
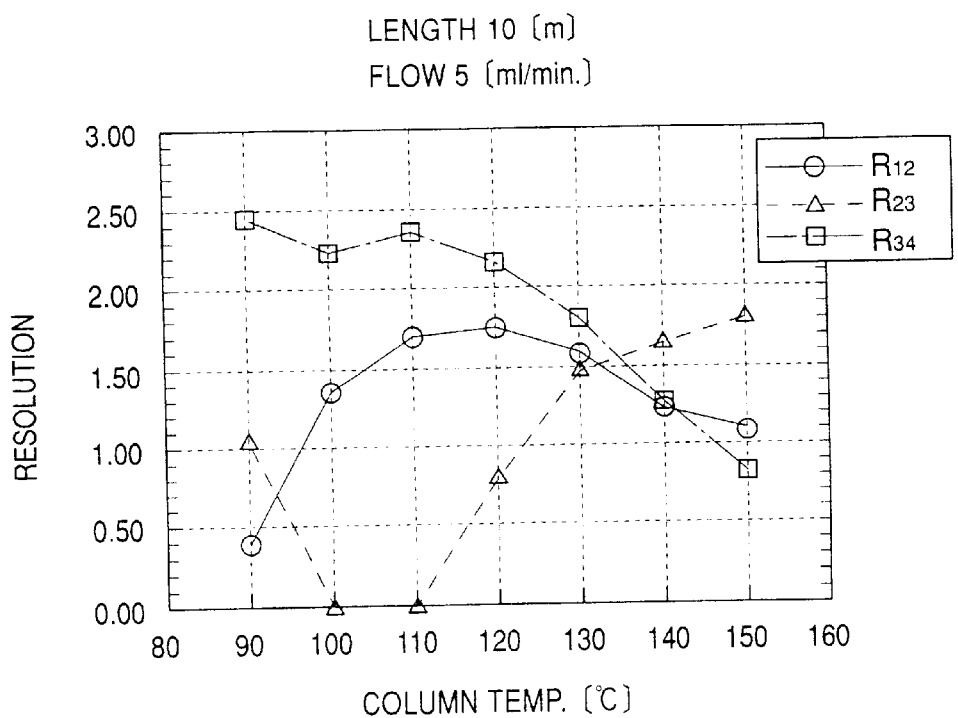
FIG. 33 is a graph illustrating resolutions for the individual constituents relative to capillary column temperature in a capillary column having a length of 10 [m] with a carrier gas flow rate kept constant at 5 [ml/min.]
Figure 34:
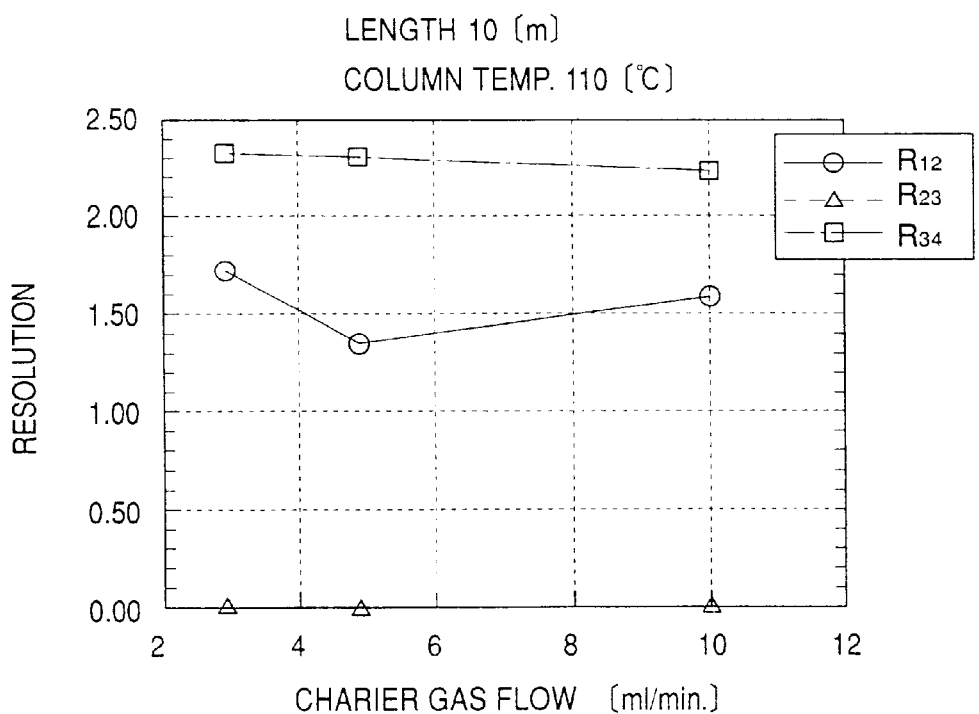
FIG. 34 is a graph illustrating resolutions for the individual constituents relative to carrier gas flow rate in a capillary column having a length of 10 [m] with a capillary column temperature kept constant at 110° C.

Pentane, main column length of 10 m:

Referring to FIG. 30, a higher column temperature results in a shorter retention time for all the three constituents. Referring to FIG. 31, with a column temperature of 110° C., a higher flow rate leads to a shorter retention time for all the three constituents. Referring to FIG. 32, with a column temperature of 130° C., a higher flow rate brings about a sudden decrease in the retention time for all the three constituents. Referring to FIG. 33, resolution of each constituent varies with the column temperature.

Referring to FIG. 33, according to the analysis of pentane, the main column temperature should preferably be within a range of from 125 to 135° C., or more preferably, 130° C. Within this temperature range, the retention time of dimethyl sulfide is longer than that of pentane (FIG. 36), this corresponding to the chromatogram shown in FIG. 29[b]. Therefore, R12 is the resolution for ethanol and pentane, and R23 is the resolution for pentane and dimethyl sulfide. The lower limit value is set at 125° C. because a temperature under 125° C. leads to an R23 of under 1.3, although R12 is over 1.5 as shown in FIG. 33. The upper limit value is set at 135° C. because a temperature over 135° C. results in an R12 value under 1.3 although R23 is over 1.5, as shown in FIG. 33.

Figure 35:
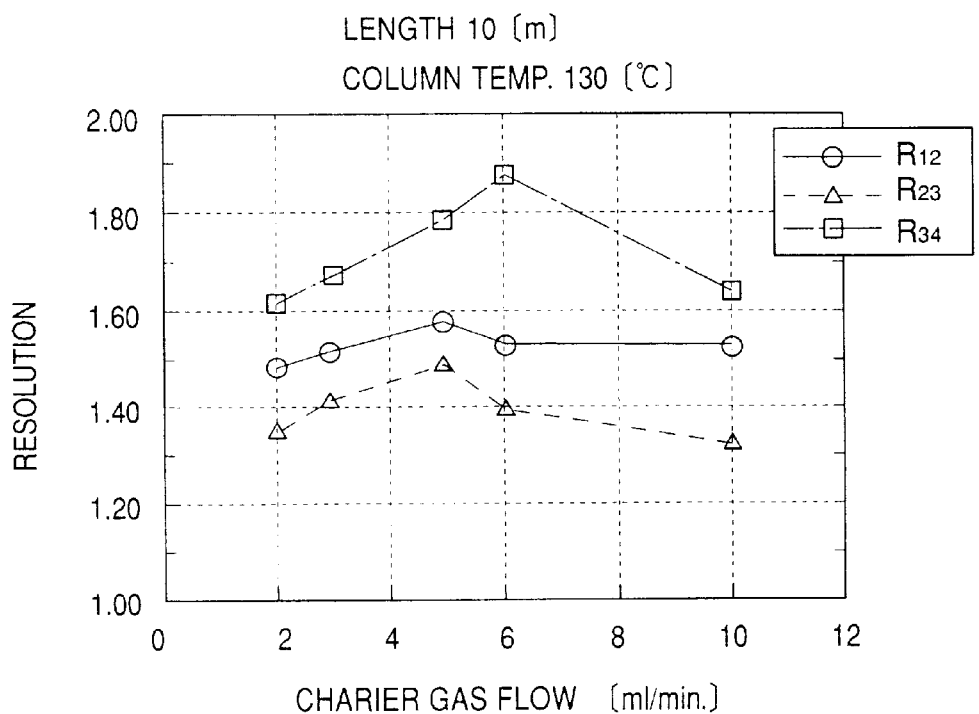
FIG. 35 is a graph illustrating resolutions for the individual constituents relative to carrier gas flow rate in a capillary column having a length of 10 [m] with a capillary column temperature kept constant at 130° C.

Referring to FIG. 35, the carrier gas flow rate should preferably be within a range of from 3 to 6 [ml/min.], or more preferably, 5 [ml/min.]. At a temperature of 130° C., the retention time of dimethyl sulfide is longer than that of pentane as shown in FIG. 36, taking the form of the chromatogram shown in FIG. 29[b]. Therefore, R12 is the resolution for ethanol and pentane, and R23 is the resolution for pentane and dimethyl sulfide. The lower limit is set at 3 [ml/min.] because a value under 3 [ml/min.] leads to an R12 of under 1.5 and an R23 of under 1.4 as shown in FIG. 35. The upper limit value is set at 6 [ml/min.] because a value of over 6 [ml/min.] results in an R23 of under 1.4 although R12 is over 1.5, as shown in FIG. 35.

FIG. 36 is a graph illustrating relative retention times for the individual constituents relative to the main column temperature. The term relative retention time as used herein means the retention time for each constituent on the assumption of a retention time of '1' for ethanol.

Pentane, main column length of 25 m:

Referring to FIG. 37, the retention time is reduced by increasing the column temperature also in the case of a column length of 25 m. Similarly, referring to FIG. 38, an increased flow rate results in a shorter retention time. Referring to FIG. 39, a higher flow rate leads to a shorter retention time also in the case of a column temperature of 110° C.

Referring to FIG. 40, resolution varies with the column temperature on the assumption of a column length of 25 m and a flow rate of 5 [ml/min.]. When analyzing pentane with a column length of 25 m, the main column temperature should preferably be within a range of from 85 to 115° C., or more preferably, from 90 to 110° C. Within this temperature range, the retention time of pentane is longer than that of dimethyl sulfide as shown in FIG. 43, resulting in a chromatogram as shown in FIG. 29[a]. Therefore, R23 is the resolution for dimethyl sulfide and pentane, and R34 is the resolution for pentane and isoprene. The lower limit value is set at 85° C. because a value under 85° C. is found to tend to result in an R34 of under 1.5 although R23 is oven 2.0 as shown in FIG. 40. The upper limit value is set at 115° C. because a temperature of over 115° C. leads to an R23 of under 1.6 although R34 is over 2.4.

The carrier gas flow rate should preferably be different between a main column temperature range of from 85 to 105° C. and a main column temperature range of from 105 to 115° C. Within the main column temperature range of from 85 to 105° C., as shown in FIG. 40, the carrier gas flow rate should preferably be within a range of from 2 to 25 [ml/min.], or more preferably, from 5 to 20 [ml/min.].

Figure 41:
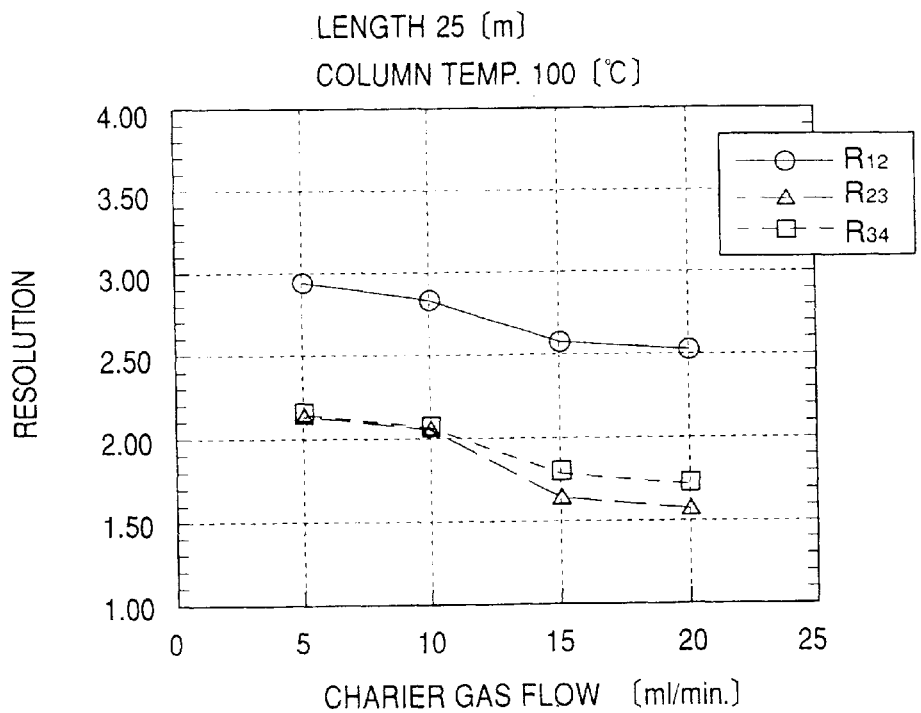
FIG. 41 is a graph illustrating resolutions for the individual constituents relative to carrier gas flow rate in a capillary column having a length of 25 [m] with a capillary column temperature kept constant at 100 ° C.
Figure 42:
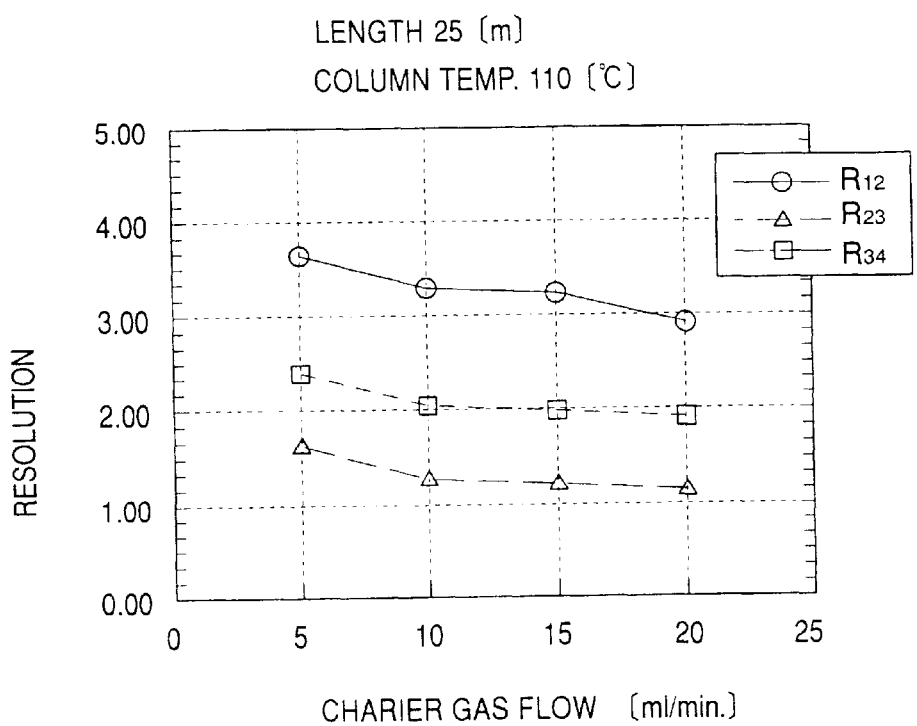
FIG. 42 is a graph illustrating resolutions for the individual constituents relative to carrier gas flow rate in a capillary column having a length of 25 [m] with a capillary column temperature kept constant at 110° C.

The upper limit value is set at 25 [ml/min.] because a flow rate of over 25 [ml/min.] causes a decrease in R23 and R34, as shown in FIG. 41. Within the main column temperature range of from 105 to 115° C., the carrier gas flow rate should preferably be within a range of from 2 to 10 [ml/min.], or more preferably, 5 [ml/min.], as shown in FIG. 42. The upper limit value is set at 10 [ml/min.] because a flow rate of over 10 [ml/min.] leads to an R23 of under 1.4 although R34 is over 2.0 as shown in FIG. 42.

Dimethyl sulfide, main column length of 10 m:

Referring again to FIG. 33, when analyzing dimethyl sulfide with a main column length of 10 m, the main column temperature should preferably be within a range of from 125 to 140° C., or more preferably, 130° C. Within this temperature range, the retention time of dimethyl sulfide is longer than that of pentane as shown in FIG. 36, resulting in a chromatogram as shown in FIG. 29[b]. Therefore, R23 is the resolution for pentane and dimethyl sulfide, and R34 is the resolution for dimethyl sulfide and isoprene. In order to ensure clear separation of dimethyl sulfide, both R23 and R34 must be at least certain values. The lower limit value is set at 125° C. because a value of under 125° C. results in an R23 of under 1.3 as shown in FIG. 33. The upper limit value is set at 140° C. because a value of over 140° C. leads to an R34 of under 1.3 as shown in FIG. 33.

In this case, the carrier gas flow rate should preferably be within a range of from 3 to 6 [ml/min.], or more preferably, 5 [ml/min.]. The lower limit value is set at 3 [ml/min.] because a value of under 3 [ml/min.] results in an R23 of under 1.4 as shown in FIG. 35. The upper limit value is set at 6 [ml/min.] because a value of over 6 [ml/min.] leads to an R23 of under 1.4 as shown in FIG. 35.

Dimethyl sulfide, main column length of 25 m:

Referring again to FIG. 40, when analyzing dimethyl sulfide with a column length of 25 m, the main column temperature should preferably be within a range of from 80 to 115° C., or more preferably, from 90 to 110° C. Within this temperature range, the retention time of pentane is longer than that of dimethyl sulfide as shown in FIG. 43, resulting in a chromatogram as shown in FIG. 29[a]. Therefore, R12 is the resolution for ethanol and dimethyl sulfide, and R23 is the resolution for dimethyl sulfide and pentane. In order to ensure clear separation of dimethyl sulfide, both R12 and R23 must be at least certain values. The lower limit value is set at 80° C. because a temperature of under 80° C. tends to give an R12 of under 1.5 as shown in FIG. 40. The upper limit value is set at 115° C. because a temperature of over 115° C. results in an R23 of under 1.6.

When analyzing dimethyl sulfide with a column length of 25 m, the carrier gas rate should preferably vary between the main column temperature range of from 80 to 105° C. and the range thereof of from 105 to 115° C. At a main column temperature within the range of from 80 to 105° C., the carrier gas flow rate should preferably be within a range of from 2 to 25 [ml/min.], or more preferably, from 5 to 20 [ml/min.] as shown in FIG. 41. At a temperature of 100° C. as shown in FIG. 23, the retention time of pentane is longer than that of dimethyl sulfide as shown in FIG. 43, resulting in a chromatogram as shown in FIG. 29[a]. Therefore, R12 is the resolution for ethanol and dimethyl sulfide, and R23 is the resolution for dimethyl sulfide and pentane. To ensure clear separation of dimethyl sulfide, both R12 and R23 must be at least a certain value. The lower limit value is set a 2 [ml/min.] because a flow rate of under 2 [ml/min.] cannot give a sufficient signal intensity. The upper limit value is set at 25 [ml/min.] because a flow rate of over 25 [ml/min.] tends to give an R23 of under 1.5 as shown in FIG. 41. At a main column temperature within the range of from 105 to 115° C., the carrier gas flow rate should preferably be within a range of from 2 to 10 [ml/min.], or more preferably, 5 [ml/min.] as shown in FIG. 42. The upper limit value is set at 10 [ml/min.] because a flow rate of over [ml/min.] results in an R23 of under 1.4.

Isoprene, main column length of 10 m:

Referring again to FIG. 33, when analyzing isoprene with a column length of 10 m, the main column temperature should preferably be within a range of from 20 to 140° C., or more preferably, from 30 to 130° C. Within this temperature range, as shown in FIG. 36, the retention time of isoprene is always longer than that of dimethyl sulfide or pentane, resulting in a chromatogram shown in FIG. 29[a] or 29[b]. Therefore, R34 is the resolution for isoprene and dimethyl sulfide or pentane. To ensure clear separation of isoprene, R34 must be at least a certain value. The lower limit value is set at 20° C. (room temperature) because a lower temperature only leads to a longer retention time as shown in FIG. 30, and is not considered to affect separation of isoprene from the other constituents as shown in FIG. 30. The upper limit value is set at 140° C. because a temperature of over 140° C. leads to an R34 of under 1.3 as shown in FIG. 33.

As shown in FIG. 35, the carrier gas flow rate should preferably be within a range of from 2 to 10 [ml/min.], or more preferably, 6 [ml/min.]. At a temperature of 130° C. as shown in FIG. 35, the retention time of dimethyl sulfide is longer than that of pentane as shown in FIG. 36, resulting in a chromatogram shown in FIG. 29[b]. Therefore, R34 is the resolution for dimethyl sulfide and isoprene. To ensure clear separation of isoprene, R34 must be at least a certain value. The lower limit value is set at 2 [ml/min.] because a flow rate of under 2 [ml/min.] leads to an R34 of under 1.6 as shown in FIG. 35. The upper limit value is set at 10 [ml/min.] because a flow rate of over 10 [ml/min.] leads to an R34 of under 1.6 as shown in FIG. 35.

Isoprene, column length of 25 m:

Referring again to FIG. 40, when analyzing isoprene in a main column having a length of 25 m, the main column temperature should preferably be within a range of from 80 to 150° C., or more preferably, from 90 to 110° C. Within this temperature range, as shown in FIG. 43, the retention time of isoprene is always longer than that of dimethyl sulfide or pentane, resulting in a chromatogram shown in FIG. 29[a] or 29[b]. Therefore, R34 is the resolution for isoprene and dimethyl sulfide or pentane. To ensure clear separation of isoprene, R34 must be at least a certain value. The lower limit value is set at 80° C. because a temperature of under 80° C. tend to give an R34 of under 1.5 as shown in FIG. 40. The upper limit value is set at 150° C. because a value of over 150° C. gives an R34 of under 1.6 as shown in FIG. 40.

As shown in FIG. 41, the carrier gas flow rate should preferably be within a range of from 2 to 25 [ml/min.], or more preferably, from 5 to 20 [ml/min.]. At a temperature of 100° C. as shown in FIG. 22, the retention time of pentane is longer than that of dimethyl sulfide as shown in FIG. 43, resulting in a chromatogram shown in FIG. 29[a]. Therefore, R34 is the resolution for pentane and isoprene. To ensure clear separation of isoprene, R34 must be at least a certain value. The lower limit value is set at 2 [ml/min.]

because a flow rate of under 2 [ml/min.] leads to unavailability of a sufficient signal intensity. The upper limit value is set at 25 [ml/min.] because a value of over 25 [ml/min.] tends to give an R34 of under 1.6 as shown in FIG. 22.

Referring to FIGS. 44 to 47, it is possible to obtain a satisfactory chromatogram at a temperature set in response to the particular use.

The results of optimization of analytical conditions have been described above for cases where main columns 14 having lengths of 10 [m] and 25 [m] are used. When considering the difference in performance of the main column 14 based on the difference in length of the main column 14, results similar to those obtained with the main column 14 having a length of 10 [m] are considered to be available under the foregoing analytical conditions even when using a main column having a length within a range of from 8 to 12 [m], and even for a main-column having a length within a range of from 20 to 30 [m], similar results as those of the main column 14 having a length of 25 [m] are considered to be available under the foregoing analytical conditions.

The above-mentioned temperature and flow rate are controlled by means of the controller 44.

The entire disclosure of Japanese patent Applications:

No. 7-270533 filed on Sep. 25, 1995;

No. 7-319553 filed on Nov. 14, 1995;

No. 8-073208 filed on Mar. 4, 1996;

No. 8-191342 filed on Jul. 2, 1996;

No. 8-231371 filed on Aug. 13, 1996;

No. 8-231372 filed on Aug. 13, 1996; and

No. 9-145846 filed on May 20, 1997, including the specification, claims, drawings and summary are incorporated herein by reference in its entirety.

What is claimed is:

1. An apparatus for analyzing a breath sample, the apparatus comprising:
   (a) desorbing apparatus for desorbing a breath sample absorbed into an absorbent sample tube;
   (b) a chromatographic precolumn for passing the breath sample desorbed from the absorbent sample tube in a retention time prescribed for each constituent;
   (c) a sample receiving tube for receiving the exhaled breath sample;
   (d) a sample loop for aspirating a prescribed quantity of breath sample from the sample receiving tube;
   (e) a chromatographic main column for passing the breath sample having passed through the precolumn or the sample loop, in a retention time prescribed for each constituent;
   (f) a detector for detecting constituents having passed through the main column;
   (g) a data processor for generating a chromatograph for the constituents detected by the detector;
   (h) a sample valve which connects the sample loop and the main column when a breath sample is aspirated into the sample loop;
   (i) a standard gas bottle for supplying a standard gas;
   (j) a standard gas valve which connects the standard gas bottle and the sample loop when testing sensitivity of the main column.

2. Apparatus according to claim 1, further comprising:
   (a) a carrier gas bottle;
   (b) a first carrier gas line for carrying the breath sample aspirated into the sample loop to the sample valve, the main column and the detector;
   (c) a second carrier gas line for carrying the breath sample desorbed from the absorbent sample tube to the sample valve, the precolumn, the main column and the detector;
   (d) a first solenoid valve provided between the first carrier gas line and the carrier gas bottle; and
   (e) a second solenoid valve provided between the second carrier gas line and the carrier gas bottle.

3. Apparatus according to claim 2, further comprising:
   (a) a third carrier gas line for carrying the standard gas aspirated into the sample loop to the sample valve, the main column and the detector; and
   (b) a third solenoid valve provided between the third carrier gas line and the standard gas bottle.

4. Apparatus according to claim 3, further comprising:
   (a) a fourth carrier gas line which carries the constituents having passed through the precolumn in the breath sample desorbed from the absorbent sample tube;
   (b) a fifth carrier gas line which purges the constituents not having passed through the precolumn in the breath sample desorbed from the absorbent sample tube; and
   (c) wherein said sample valve comprises:
      (i) a first operating position for selecting said second carrier gas line; and
      (ii) a second operating position for selecting said fourth and the fifth carrier gas lines.

5. Apparatus according to claim 4, further comprising:
   (a) a detector heater for heating the detector; and
   (b) a column heater for heating the precolumn and the main column.

6. Apparatus according to claim 5, further comprising:
   (a) a controller having a temperature control unit for heating the detector heater and the column heater to a predetermined temperature prior to starting analysis.

7. The apparatus of claim 6, wherein the standard gas comprises hexane and pentane.

8. Apparatus according to claim 6, further comprising:
   (a) input apparatus comprising:
      (i) a start button for instructing start;
      (ii) an analysis start button for instructing start of analysis;
      (iii) a shutdown button for instructing shutdown; and
      (iv) a test button for instructing a test; and
   (b) wherein said controller comprises:
      (i) a start controller which purges said columns when receiving a start signal from the start button and heats said detector heater and said column heater to a predetermined temperature;
      (ii) an analysis controller which desorbs a breath sample or aspirates a breath when receiving an analysis start signal from the analysis start button and switches over said first to fifth gas lines;
      (iii) a shutdown controller which reduces temperature of said detector heater and said column heater and discontinues supply of the carrier gas when receiving a shutdown signal from the shutdown button; and
      (iv) a test controller which tests sensitivity and resolution of the detector with the standard gas when receiving a test signal from the test button.

9. Apparatus according to claim 8, further comprising:
   (a) a display connected to the controller;
   (b) said start controller displaying a message of preparation completion on the display upon completion of start controller; and
   (c) said test controller displaying a message of test result on the display upon completion of test controller.

10. Apparatus according to claim 1, wherein said desorbing apparatus comprises:
(a) an absorbent sample tube heater which heats the absorbent sample tube to desorb the breath sample absorbed in said absorbent sample tube;
(b) a secondary concentrating tube for absorbing the breath sample in the interior thereof;
(c) a secondary concentrating tube cooler which cools the secondary concentrating tube for absorbing into said secondary concentrating tube the breath sample desorbed from said absorbent sample tube; and
(d) a secondary concentrating tube heater which heats the secondary concentrating tube for desorbing the breath sample absorbed in said secondary concentrating tube.

11. Apparatus according to claim 1, wherein:
(a) said data processor comprises apparatus for subjecting the detection result of said standard gas to a data processing to calculate sensitivity and resolution of the main column.

12. Apparatus according to claim 1, further comprising:
(a) a rotary valve having ten ports and lines for connecting adjacent ports;
(b) a carrier gas bottle;
(c) a first carrier gas line which connects the carrier gas bottle and the desorbing means;
(d) a first valve provided in the first carrier gas line;
(e) a second carrier gas line which connects the carrier gas bottle and ports of said rotary valve;
(f) a second valve provided in the second carrier gas line;
(g) said ports being connected sequentially from the first port:
  (i) an end of the precolumn;
  (ii) an end of the main column;
  (iii) an end of the sample loop;
  (iv) a pump;
  (v) the sample receiving tube;
  (vi) the other end of the sample loop;
  (vii) the second carrier gas line;
  (viii) a vent;
  (ix) the other end of the precolumn; and
  (x) the desorber;
(h) said rotary valve having a first operating position and a second operating position;
  (i) the first operating position connecting:
    an end of the precolumn and an end of the main column;
    an end of the sample loop and the pump;
    the sample receiving tube and the other end of the sample loop;
    the second carrier gas line and the vent; and
    the other end of the precolumn and the desorber; and
  (ii) the second operating position connecting:
    the desorber and an end of the precolumn;
    an end of the main column and an end of the sample loop;
    the pump and the sample receiving tube;
    the other end of the sample loop and the second carrier gas line; and
    the vent and the other end of the precolumn.

13. An apparatus for analyzing a breath sample, the apparatus comprising:
(a) desorbing apparatus for desorbing a breath sample absorbed in an absorbent sample tube:
(b) a chromatographic precolumn for passing the breath sample desorbed from the absorbent sample tube in a retention time prescribed for each constituent;
(c) a sample receiving tube receiving the breath sample;
(d) a sample loop aspirating the breath sample from the sample receiving tube;
(e) a chromatographic main column for passing the breath sample having passed through the precolumn or the sample loop, in a retention time prescribed for each constituent;
(f) a column heater which heats the main column and the precolumn to a prescribed temperature;
(g) a detector detecting the constituents having passed through the main column;
(h) a detector heater heating the detector to a preselected temperature;
(i) a data processor generating a chromatograph of the constituents detected by the detector;
(j) a sample valve which connects the sample loop and the main column when a breath sample is aspirated into the sample loop; and
(k) a controller comprising:
  (i) column heat control apparatus which heats said column heater to a preselected temperature in response to the length of the main column;
  (ii) detector heat control apparatus for heating the detector to a preselected temperature; and
  (iii) completion timing apparatus for setting completion timing of analysis with reference to the retention time in response to a preselected temperature and the object of analysis.

14. An apparatus for analyzing a breath sample, the apparatus comprising:
(a) desorbing apparatus for desorbing breath sample absorbed into an absorbent sample tube:
(b) a chromatographic precolumn for passing breath sample desorbed from the absorbent sample tube in a retention time prescribed for each constituent;
(c) a sample receiving tube receiving exhaled breath sample;
(d) a sample loop for aspirating a prescribed quantity of breath sample from the sample receiving tube;
(e) a chromatographic main column for passing breath sample having passed through the precolumn or the sample loop, in a retention time prescribed for each constituent;
(f) a detector for detecting constituents having passed through the main column;
(g) a data processor for generating a chromatograph for the constituents detected by the detector;
(h) a sample valve comprising a first position which connects the sample loop and the main column when breath sample is aspirated into the sample loop and a second position which connects the precolumn to the main column;
(i) a standard gas bottle for supplying a standard gas;
(j) a standard gas valve which connects the standard gas bottle and the sample loop when testing sensitivity of the main column.

* * * * *

UNITED STATES PATENT AND TRADEMARK OFFICE
CERTIFICATE OF CORRECTION

PATENT NO. : 6,341,520 B1
DATED : January 29, 2002
INVENTOR(S) : Katsuhiko Satoh et al.

It is certified that error appears in the above-identified patent and that said Letters Patent is hereby corrected as shown below:

<u>Title page,</u>
Item [56], References Cited, OTHER PUBLICATIONS, the following were omitted and should be included:
--      Driscoll, "Applications of a photoionization detector in gas chromatography," American Laboratory, vol. 8, No. 10, pp. 71-75.
        Cailleux et al., Free Radical Research Communications, Vol. 18, No. 6, pages 323-327, 1993, "Is Pentane a Normal Constituent of Human Breath?" --

Signed and Sealed this

Twelfth Day of November, 2002

Attest:

Attesting Officer

JAMES E. ROGAN
Director of the United States Patent and Trademark Office